US010803555B2

(12) United States Patent
Song et al.

(10) Patent No.: US 10,803,555 B2
(45) Date of Patent: Oct. 13, 2020

(54) SYSTEM AND METHOD FOR DETERMINING A TRAINED NEURAL NETWORK MODEL FOR SCATTERING CORRECTION

(71) Applicant: SHANGHAI UNITED IMAGING HEALTHCARE CO., LTD., Shanghai (CN)

(72) Inventors: Yanli Song, Shanghai (CN); Xin Zhou, Shanghai (CN); Xiaodan Xing, Shanghai (CN); Gang Chen, Shanghai (CN); Qiang Li, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 7 days.

(21) Appl. No.: 16/042,536

(22) Filed: Jul. 23, 2018

(65) Prior Publication Data

US 2019/0066268 A1   Feb. 28, 2019

(30) Foreign Application Priority Data

Aug. 31, 2017  (CN) .......................... 2017 1 0772800
Aug. 31, 2017  (CN) .......................... 2017 1 0775674

(51) Int. Cl.
*G06T 5/00* (2006.01)
*G06N 3/08* (2006.01)
(Continued)

(52) U.S. Cl.
CPC .......... *G06T 5/002* (2013.01); *G06N 3/0454* (2013.01); *G06N 3/08* (2013.01); *A61B 6/5282* (2013.01);
(Continued)

(58) Field of Classification Search
CPC .......... G06T 5/002; G06T 2207/20084; G06T 2207/10116; G06T 2207/10081;
(Continued)

(56) References Cited

U.S. PATENT DOCUMENTS 1,164,987 A    12/1915  Bucky
8,184,767 B2    5/2012  Mishra et al.
(Continued)

FOREIGN PATENT DOCUMENTS

CN    105068138 A    11/2015
CN    106845440 A    6/2017
(Continued)

OTHER PUBLICATIONS

Takahiro Kawamura et al. improvement in image quality and workflow of X-ray examinations using a new image processing method, "virtural grid technology". *Fujifilm Research& Development*(60): 21-27(2015).

(Continued)

*Primary Examiner* — Nizar N Sivji
(74) *Attorney, Agent, or Firm* — Metis IP LLC

(57) ABSTRACT

A method for generating a trained neural network model for scanning correction corresponding to one or more imaging parameters is provided. The trained neural network model may be trained using training data. The training data may include at least one first set of training data. The first set of training data may be generated according to a process for generating the first set of training data. The process may include obtaining a first image and a second image corresponding to the one or more imaging parameters. The second image may include less scattering noises than the first image. The process may further include determine the first set of training data based on the first image and the second image.

20 Claims, 14 Drawing Sheets

(51) Int. Cl.
*G06N 3/04* (2006.01)
*A61B 6/00* (2006.01)
(52) U.S. Cl.
CPC ............... *G06T 2207/10081* (2013.01); *G06T 2207/10088* (2013.01); *G06T 2207/10104* (2013.01); *G06T 2207/10116* (2013.01); *G06T 2207/20081* (2013.01); *G06T 2207/20084* (2013.01)
(58) Field of Classification Search
CPC .......... G06T 2207/20081; G06T 2207/10104; G06T 2207/10088; G06N 3/0454; G06N 3/08; G06N 3/0481; G06N 7/005; G06N 3/0445

See application file for complete search history.

(56) References Cited

U.S. PATENT DOCUMENTS

| | | | |
|---|---|---|---|
| 8,768,037 B2 | 7/2014 | Kruschel et al. | |
| 2009/0202127 A1 | 8/2009 | Bertram et al. | |
| 2010/0046822 A1 | 2/2010 | Li et al. | |
| 2012/0148156 A1* | 6/2012 | Sehnert | A61B 6/4291 382/171 |
| 2018/0146935 A1* | 5/2018 | Song | G06T 5/002 |

FOREIGN PATENT DOCUMENTS

| | | |
|---|---|---|
| CN | 106952239 A | 7/2017 |
| DE | 102012217965 A1 | 4/2014 |

OTHER PUBLICATIONS

Detlef Mentrup et al. Grid-like contrast restoration for non-grid chest radiographs by software-based scatter correction. ECR2014_C-0181, 2014. 15 pages.

Ernst-Peter Rührnschopf et al. A general framework and review of scatter correction methods in x-ray cone beam computer tomography. Part1: Scatter compensation approaches, *Medical Physics*, 38(7): 4296-4311(2011).

Chrisriaan Fivez et al. Multi-resolution contrast amplification in digital radiography with compensation for scattered radiation. International Conference on Image Processing(1): 339-342(1996).

Carey E. Floyd et al. Scatter compensation in digital chest radiography using fourier deconvolution. Investigative Radiology 24 (1): 30-33(1989).

Chao Dong et al. Learning a deep convolutional network for image super-resolution. ECCV 2014, Part IV, LNCS 8692, pp. 184-199(2014).

Kai Zhang et al. Beyond a Gaussian denoiser_residual learning of deep CNN for image denoising. airXiv: 1608.03981v1[cs.CV]Aug. 13, 2016, 13 pages.

Yo Seob Han et al. Deep residual learning for compressed sensing CT reconstruction via persistent homology analysis. arXiv: 1611.06391v2 [cs.CV] Nov. 25, 2016, 10 pages.

First Office Action in Chinese Application No. 201710772800.9 dated Apr. 7, 2020, 23 Pages.

* cited by examiner

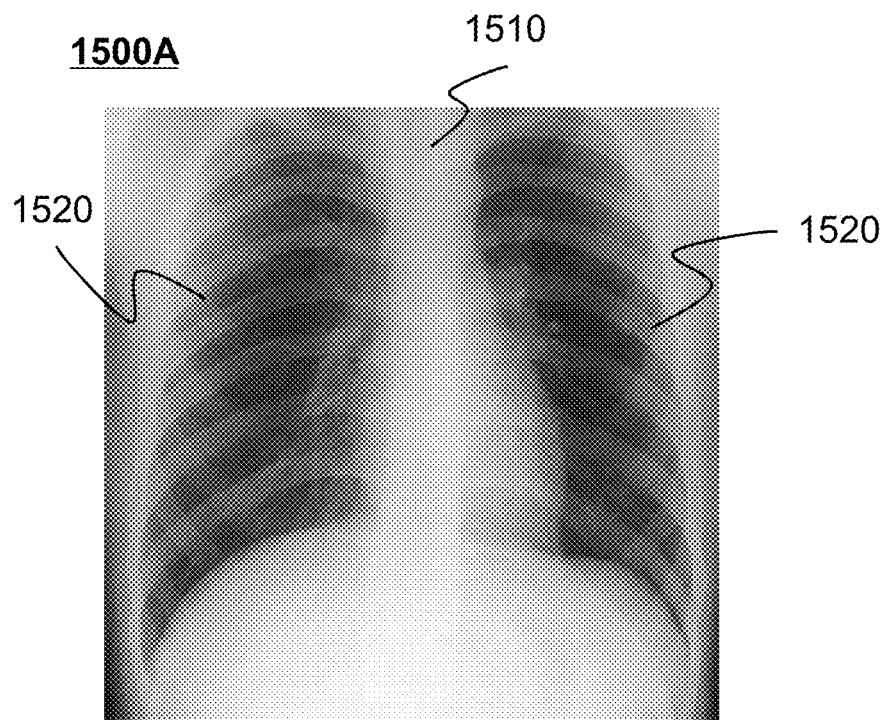
FIG. 15-A
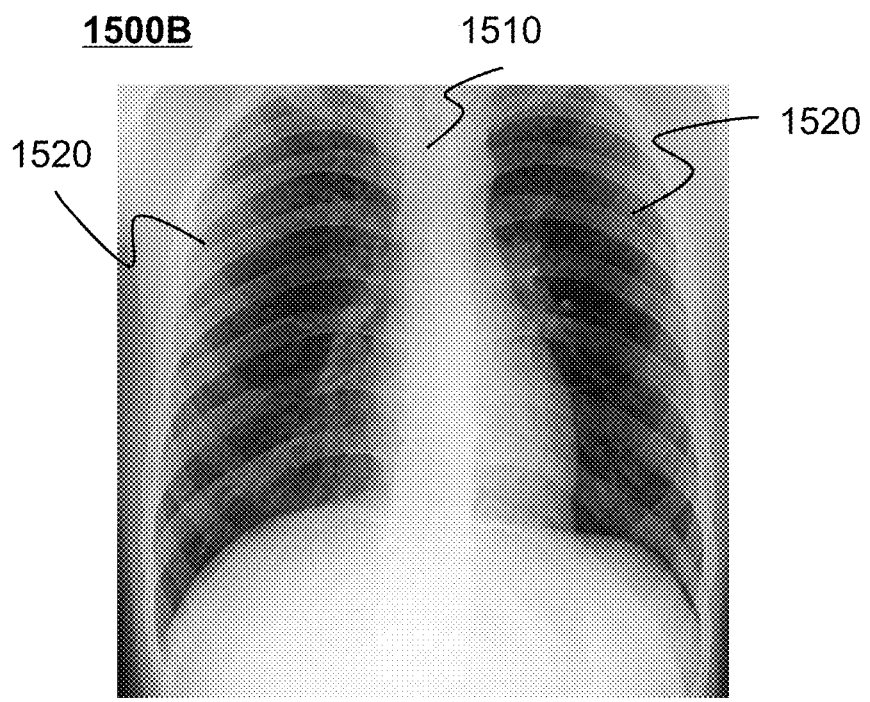
FIG. 15-B

SYSTEM AND METHOD FOR DETERMINING A TRAINED NEURAL NETWORK MODEL FOR SCATTERING CORRECTION

CROSS-REFERENCE TO RELATED APPLICATIONS

This application claims priority to Chinese Patent Application No 201710772800.9, filed on Aug. 31, 2017, and Chinese Patent Application No 201710775674.2, filed on Aug. 31, 2017. Each of the above-referenced applications is expressly incorporated herein by reference in their entireties.

TECHNICAL FIELD

The present disclosure generally relates to image processing, and more specifically, relates to systems and methods for reducing scattering noises in an image based on a model.

BACKGROUND

High-energy rays (e.g., X-rays, y-rays) are widely used in medical imaging. For example, X-rays are used in, for example, computed tomography (CT) devices or digital radiography (DR) devices to generate an image of a subject. During a scan, X-rays irradiated on the subject may pass through the subject and be detected by a detector. However, some X-rays may scatter when passing through the subject, which may cause scattering noises in the image generated based on the scan. Thus, it is desirable to provide mechanisms for correcting an image to reduce or eliminate scattering noises.

SUMMARY

In one aspect of the present disclosure, a system is provided. The system may include a storage device, and at least one processor configured to communicate with the storage device. The storage device may store a set of instructions. When executing the set of instructions, the at least one processor may be configured to direct the system to generate a trained neural network model for scattering correction corresponding to one or more imaging parameters. The trained neural network model may be trained using training data. The training data may include at least one first set of training data. The first set of training data may be generated according to a process for generating the first set of training data. The process may include obtaining a first image corresponding to the one or more imaging parameters, and obtaining a second image. The second image may include less scattering noises than the first image. The process may further include determining the first set of training data based on the first image and the second image.

In some embodiments, the second image may be generated according to second scan data acquired by an imaging device configured with a grid under the one or more imaging parameters, and the first image may be generated according to first scan data acquired by the imaging device without the grid under the one or more imaging parameters. Alternatively, the first image may be generated according to the first scan data acquired by the imaging device without the grid under the one or more imaging parameters, and the second image may be generated based on the first image by removing at least some of the scattering noises of the first image. Alternatively, the first image and the second image may be simulated according to a Monte-Carlo technique under the one or more imaging parameters.

In some embodiments, the determining the first set of training data based on the first image and the second image may further include processing the first image and the second image, and determining the first set of training data based on the processed first image and the processed second image.

In some embodiments, the first set of training data may include input data and tag data. The determining the first set of training data may include selecting a first sub-area from the first image, and designating image data related to the first sub-area as the input data. The determining the first set of training data may further include selecting a second sub-area corresponding to the first sub-area from the second image, and designating image data related to the second sub-area as the tag data.

In some embodiments, to generate the trained neural network model for scattering correction, the at least one processor may be further configured to direct the system to acquire a preliminary neural network model. The at least one processor may be further configured to direct the system to determine one or more model parameters by inputting the training data into the preliminary neural network model. The at least one processor may be further configured to direct the system to determine the trained neural network model based on the one or more model parameters and the preliminary neural network model.

In some embodiments, the first set of training data may include input data and tag data. The one or more model parameters may include a relationship between the input data and the tag data.

In some embodiments, to determine the one or more model parameters, the at least one processor may be configured to direct the system to divide the input data into a plurality of first data blocks, and divide the tag data into a plurality of second data blocks corresponding to the plurality of first data blocks. The at least one processor may be further configured to direct the system to determine first gradient information of the first data blocks, and determine second gradient information of the second data blocks. The at least one processor may be further configured to direct the system to determine the relationship between the input data and the tag data based on the first gradient information and the second gradient information.

In some embodiments, the determining the first set of training data based on the first image and the second image may include decomposing the first image into a plurality of sets of first decomposition data, and decomposing the second image into a plurality of sets of second decomposition data. The number of the plurality of sets of first decomposition data may be equal to the number of the plurality of sets of second decomposition data. The determining the first set of training data may further include generating a plurality of matching pairs of decomposition data based on the plurality of sets of first decomposition data and the plurality of sets of second decomposition data. Each of the plurality of matching pairs of decomposition data may include a set of first decomposition data and a corresponding set of second decomposition data. The determining the first set of training data may further include determining the first set of training data based on one of the plurality of matching pair of decomposition data.

In some embodiments, the decomposing of the first image may be performed according to a frequency of the at least of the first image or image data related to the first image. The decomposing of the second image may be performed according to a frequency of the at least one of the second image or image data related to the second image.

In some embodiments, the decomposing of the first image may be performed according to at least one of a wavelet decomposition technique or a Laplacian decomposition technique. The decomposing of the second image may be performed according to at least one of the wavelet decomposition technique or the Laplacian decomposition technique.

In some embodiments, the plurality of sets of first decomposition data may include a plurality of first decomposed images corresponding to a plurality of frequency bands. The plurality of sets of second decomposition data may include a plurality of second decomposed images corresponding to the plurality of frequency bands. To generate the trained neural network model for scattering correction, the at least one processor may be further configured to direct the system to determine a relationship between a first decomposed image corresponding to the frequency band and a second decomposed image corresponding to the frequency band for each of the plurality of frequency bands. The at least one processor may be further configured to direct the system to determine the trained neural network model for scattering correction based on the determined relationships for the plurality of frequency bands.

In another aspect of the present disclosure, a system is provided. The system may include a storage device, and at least one processor configured to communicate with the storage device. The storage device may store a set of instructions. When executing the set of instructions, the at least one processor may be configured to direct the system to obtain a target image and one or more target imaging parameters corresponding to the target image. The at least one processor may be also configured to obtain one or more trained neural network models for scattering correction corresponding to one or more sets of imaging parameters. The at least one processor may be further configured to select a target trained neural network model for scattering correction corresponding to the one or more target imaging parameters among the one or more trained neural network models for scattering correction. The at least one processor may be further configured to correct the target image using the target trained neural network model for scattering correction.

In some embodiments, one of the one or more trained neural network model for scattering correction may be trained using training data. The training data may include at least one first set of training data. The first set of training data may be generated by a process for generating a first set of training data. The process may include obtaining a first image corresponding to the one or more imaging parameters. The process may also include obtaining a second image. The second image may include less scattering noises than the first image. The process may further include determining the first set of training data based on the first image and the second image.

In some embodiments, to correct the target image, the at least one processor may be further configured to direct the system to decompose the target image into a plurality of decomposed target images corresponding to a plurality of frequency bands. The at least one processor may be further configured to direct the system to correct the plurality of decomposed target images based on the target trained neural network model. The at least one processor may be further configured to generate the corrected target image based on the plurality of corrected decomposed target images.

In yet another aspect of the present disclosure, a method is provided. The method may be implemented on a computing device including a storage device and at least one processor. The method may include generating a trained neural network model for scattering correction corresponding to one or more imaging parameters. The trained neural network model may be trained using training data. The training data may include at least one first set of training data. The first set of training data may be generated according to a process for generating the first set of training data. The process may include obtaining a first image corresponding to the one or more imaging parameters. The process may also include obtaining a second image. The second image may include less scattering noises than the first image. The process may further include determining the first set of training data based on the first image and the second image.

In yet another aspect of the present disclosure, a method is provided. The method may be implemented on a computing device including a storage device and at least one processor. The method may include obtaining a target image and one or more target imaging parameters corresponding to the target image. The method may further include obtaining one or more trained neural network models for scattering correction corresponding to one or more sets of imaging parameters. The method may also include selecting a target trained neural network model for scattering correction corresponding to the one or more target imaging parameters among the one or more trained neural network models for scattering correction. The method may further include correcting the target image using the target trained neural network model for scattering correction.

In yet another aspect of the present disclosure, a non-transitory computer-readable storage medium is provided. The non-transitory computer-readable storage medium store instructions, when executed by at least one processor of a system, cause the system to perform a method. The method may include generating a trained neural network model for scattering correction corresponding to one or more imaging parameters. The trained neural network model may be trained using training data. The training data may include at least one first set of training data. The first set of training data may be generated according to a process for generating the first set of training data. The process may include obtaining a first image corresponding to the one or more imaging parameters. The process may also include obtaining a second image. The second image may include less scattering noises than the first image. The process may further include determining the first set of training data based on the first image and the second image.

In yet another aspect of the present disclosure, a non-transitory computer-readable storage medium is provided. The non-transitory computer-readable storage medium store instructions, when executed by at least one processor of a system, cause the system to perform a method. The method may include obtaining a target image and one or more target imaging parameters corresponding to the target image. The method may further include obtaining one or more trained neural network models for scattering correction corresponding to one or more sets of imaging parameters. The method may also include selecting a target trained neural network model for scattering correction corresponding to the one or more target imaging parameters among the one or more trained neural network models for scattering correction. The method may further include correcting the target image using the target trained neural network model for scattering correction.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 15A shows an exemplary image according to some embodiments of the present disclosure; and FIG. 15B shows an exemplary corrected image according to some embodiments of the present disclosure.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is to describe particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by another expression if they achieve the same purpose.

Figure 2:
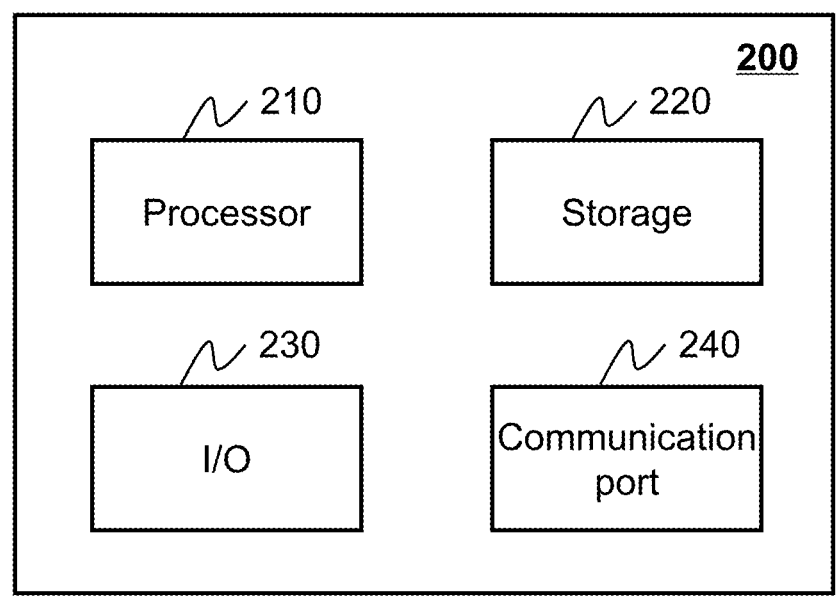
FIG. 2 is a schematic diagram illustrating exemplary hardware and/or software components of an exemplary computing device on which the processing device may be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2 and/or the central processing unit (CPU) 340 illustrated in FIG. 3) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM.

It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

An aspect of the present disclosure relates to systems and methods for correcting scattering noises of images. In order to provide a more efficient way of scattering correction, the systems and methods in the present disclosure may determine a trained neural network model for scattering correction corresponding to one or more certain imaging parameters. The trained neural network model corresponding to the certain imaging parameter(s) may be used to correct images that are acquired under the same or substantially same imaging parameter(s). To this end, the systems and methods may generate the trained neural network model by training a preliminary neural network model using training data. The training data may include at least one first set of training data. To generate a first set of training data, the systems and methods may obtain a first image and a second image corresponding to the same one or more imaging parameter(s). The second image may include less scattering noises than the first image. The systems and methods may determine the first set of training data based on the first image and the second image. Exemplary imaging parameters may include a tube voltage, a tube current, a scanning time, an irradiation dose, a slice thickness of scanning, or the like, or any combination thereof.

The following description is provided to help better understand the generation of a trained neural network model. This is not intended to limit the scope the present disclosure. For persons having ordinary skills in the art, a certain amount of variations, changes, and/or modifications may be deducted under the guidance of the present disclosure. Those variations, changes, and/or modifications do not depart from the scope of the present disclosure.

Figure 1:
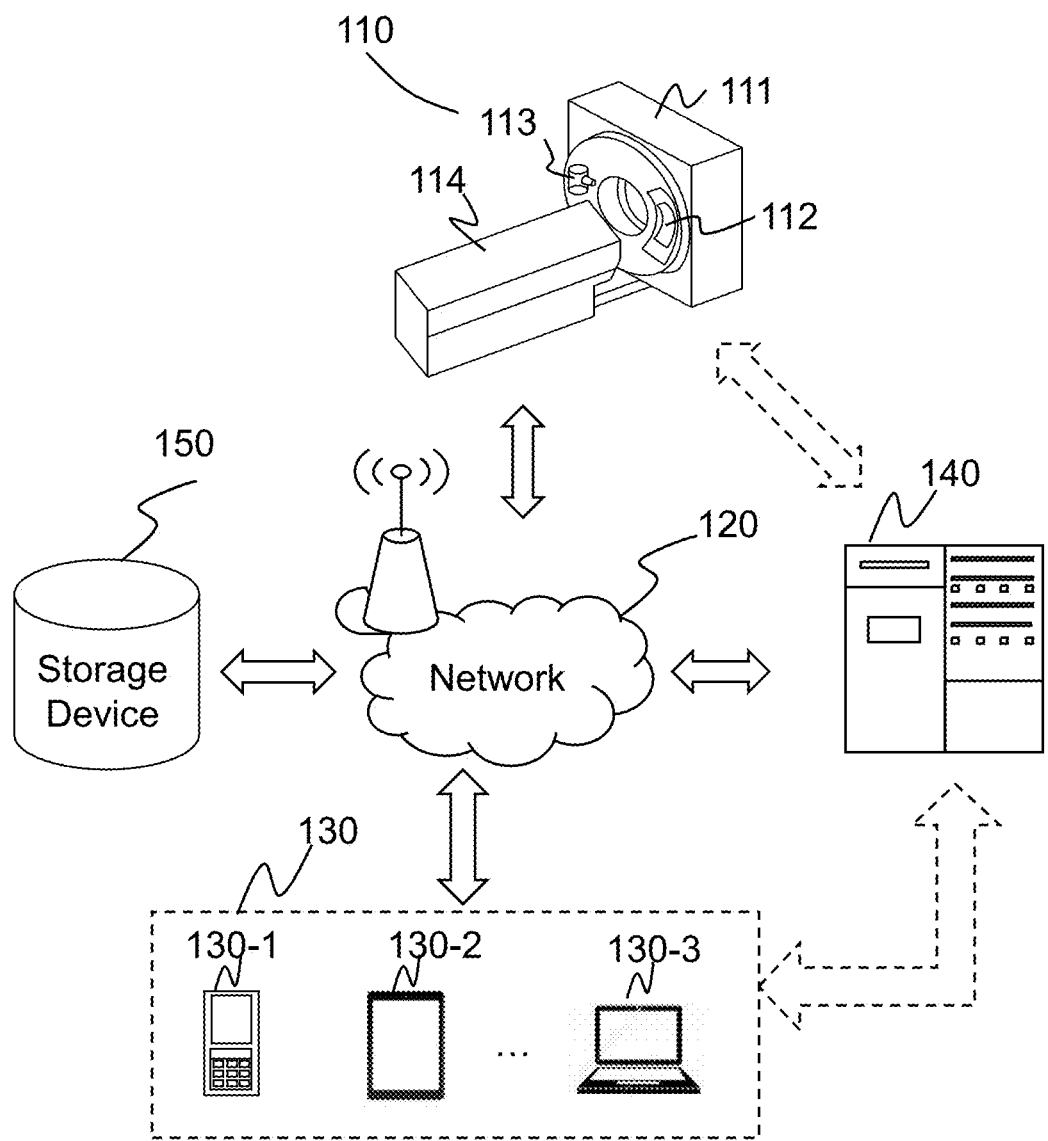
FIG. 1 is a schematic diagram illustrating an exemplary imaging system according to some embodiments of the present disclosure.

FIG. 1 is a schematic diagram illustrating an exemplary imaging system 100 according to some embodiments of the present disclosure. In some embodiments, the imaging system 100 may be a computed tomography (CT) system, a cone beam CT (CBCT) system, a computed radiography (CR) system, a digital radiography (DR) system, a digital subtraction angiography (DSA) system, a molti-modality system, or the like, or any combination thereof. Examplary multi-modality systems may include a computed tomography-positron emission tomography (CT-PET) system, a computed tomography-magnetic resonance imaging (CT-MRI) system, etc.

As illustrated in FIG. 1, the imaging system 100 may include an imaging device 110, a network 120, one or more terminal(s) 130, a processing device 140, and a storage device 150. The components in the imaging system 100 may be connected in one or more of various ways. Merely by way of example, as illustrated in FIG. 1, the imaging device 110 may be connected to the processing device 140 through the network 120. As another example, the imaging device 110 may be connected to the processing device 140 directly as indicated by the bi-directional arrow in dotted lines linking the imaging device 110 and the processing device 140. As a further example, the storage device 150 may be connected to the processing device 140 directly or through the network 120. As still a further example, the terminal(s) 130 may be connected to the processing device 140 directly (as indicated by the bi-directional arrow in dotted lines linking the terminal 130 and the processing device 140) or through the network 120.

The imaging device 110 may be configured to scan a subject and generate imaging data used to generate one or more images relating to the subject. The imaging device 110 may include a gantry 111, a detector 112, a radiation source 113, and a scanning table 114. The detector 112 and the radiation source 113 may be oppositely mounted on the gantry 111. A subject may be placed on the scanning table 114 and moved into a detection tunnel of the imaging device 110 for scan. The subject may be a biological subject (e.g., a patient, an animal) or a non-biological subject (e.g., a human-made subject). In the present disclosure, "object" and "subject" are used interchangeably.

The radiation source 113 may emit X-rays to toward the subject during the scan. The detector 112 may detect radiations (e.g., X-rays) emitted from the radiation source 113. In some embodiments, the detector 112 may include a plurality of detector units. The detector units may include a scintillation detector (e.g., a cesium iodide detector) or a gas detector. The detector units may be arranged in a single row or multiple rows. In some embodiments, the imaging device 110 may include one or more components configured to prevent or reduce radiation scatterings during a scan. For example, the imaging device 110 may include a grid (e.g., a metal grid), a slit, a beam stop array (BSA), a beam attenuation grid (BAG), and/or any other component that may prevent or reduce radiation scatterings.

The network 120 may include any suitable network that can facilitate the exchange of information and/or data for the imaging system 100. In some embodiments, one or more components in the imaging system 100 (e.g., the imaging device 110, the terminal 130, the processing device 140, or the storage device 150) may communicate information and/or data with another component(s) of the imaging system 100 via the network 120. For example, the processing device 140 may obtain image data from the imaging device 110 via the network 120. As another example, the processing device 140 may obtain user instructions from the terminal(s) 130 via the network 120.

In some embodiments, the network 120 may be any type of wired or wireless network, or a combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

The terminal(s) 130 include a mobile device 130-1, a tablet computer 130-2, a laptop computer 130-3, or the like, or any combination thereof. In some embodiments, the mobile device 130-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a smart bracelet, smart footgear, a pair of smart glasses, a smart helmet, a smartwatch, smart clothing, a smart backpack, a smart accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include Google Glasses, an Oculus Rift, a Hololens, a Gear VR, etc.

In some embodiments, the terminal(s) 130 may remotely operate the imaging device 110. In some embodiments, the terminal(s) 130 may operate the imaging device 110 via a wireless connection. In some embodiments, the terminal(s) 130 may receive information and/or instructions inputted by a user, and send the received information and/or instructions to the imaging device 110 or to the processing device 140 via the network 120. In some embodiments, the terminal(s) 130 may receive data and/or information from the processing device 140. In some embodiments, the terminal(s) 130 may be part of the processing device 140. In some embodiments, the terminal(s) 130 may be omitted.

The processing device 140 may process data and/or information obtained from the imaging device 110, the terminal 130, and/or the storage device 150. For example, the processing device 140 may train a preliminary neural network model using training data to generate a trained neural network model for scattering correction. In some embodiments, the processing device 140 may be a single server, or a server group. The server group may be centralized, or distributed. In some embodiments, the processing device 140 may be local or remote. For example, the processing device 140 may access information and/or data stored in the imaging device 110, the terminal 130, and/or the storage device 150 via the network 120. As another example, the processing device 140 may be directly connected to the imaging device 110, the terminal 130, and/or the storage device 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 200 having one or more components illustrated in FIG. 2 in the present disclosure.

The storage device 150 may store data and/or instructions. In some embodiments, the storage device 150 may store data obtained from the terminal(s) 130 and/or the processing device 140. In some embodiments, the storage device 150 may store data and/or instructions that the processing device 140 may execute or use to perform exemplary methods described in the present disclosure. In some embodiments, the storage device 150 may include a mass storage device, removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components in the imaging system 100 (e.g., the processing device 140, the terminal(s) 130, etc.). One or more components in the imaging system 100 may access the data or instructions stored in the storage device 150 via the network 120. In some embodiments, the storage device 150 may be directly connected to or communicate with one or more components in the imaging system 100 (e.g., the processing device 140, the terminal(s) 130, etc.). In some embodiments, the storage device 150 may be part of the processing device 140.

FIG. 2 is a schematic diagram illustrating exemplary hardware and/or software components of an exemplary computing device 200 on which the processing device 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (program code) and perform functions of the processing device 140 in accordance with techniques described herein. The computer instructions may include, for example, routines, programs, objects, components, signals, data structures, procedures, modules, and functions, which perform particular functions described herein. For example, the processor 210 may process data and/or image obtained from the imaging device 110, the terminal 130, the storage device 150, and/or any other component in the imaging system 100. As another example, the processor 210 may determine a set of training data based on a first image and a second image of the same subject. As yet another example, the processor 210 may train a preliminary neural network model using training data to generate a trained neural network model for scattering correction. As still another example, the processor 210 may correct a target image based on a trained neural network model for scattering correction.

In some embodiments, the processor 210 may perform instructions obtained from the terminal(s) 130. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information obtained from the imaging device 110, the terminal(s) 130, the storage device 150, or any other component of the imaging system 100. In some embodiments, the storage 220 may include a mass storage device, removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure.

The I/O 230 may input or output signals, data, and/or information. In some embodiments, the I/O 230 may enable a user interaction with the processing device 140. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected to a network (e.g., the network 120) to facilitate data communications. The communication port 240 may establish connections between the processing device 140 and the imaging device 110, the terminal(s) 130, or the storage device 150. The connection may be a wired connection, a wireless connection, or combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
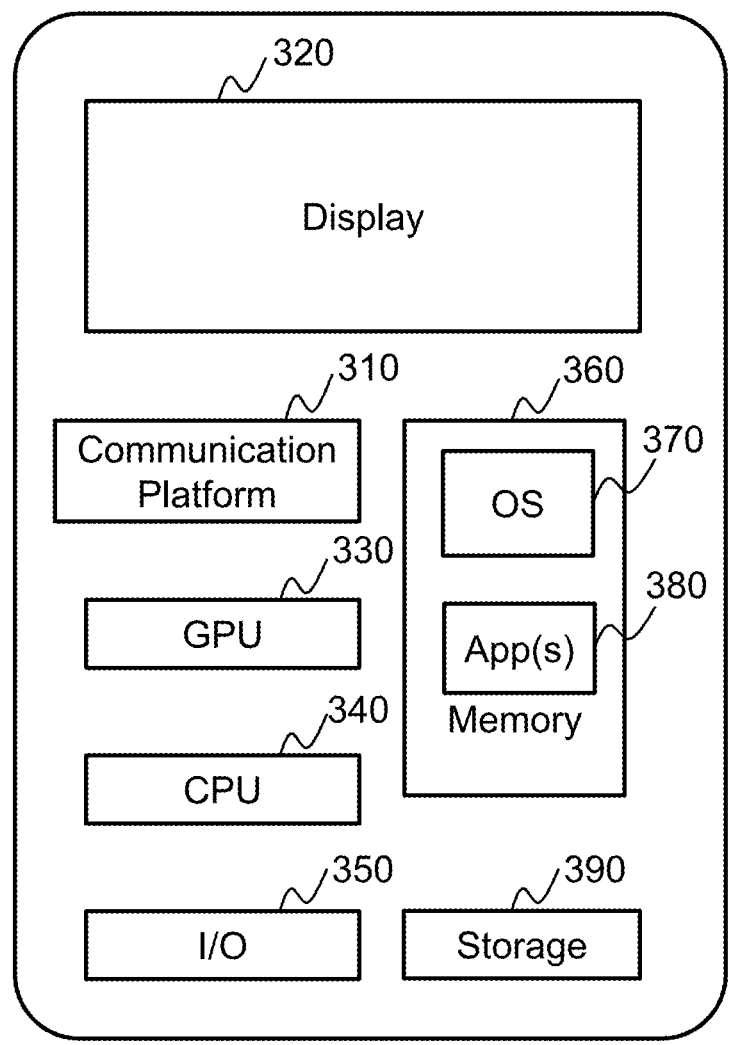
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device 300 according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the imaging system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to determine a trained neural network model as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

Figure 4A:
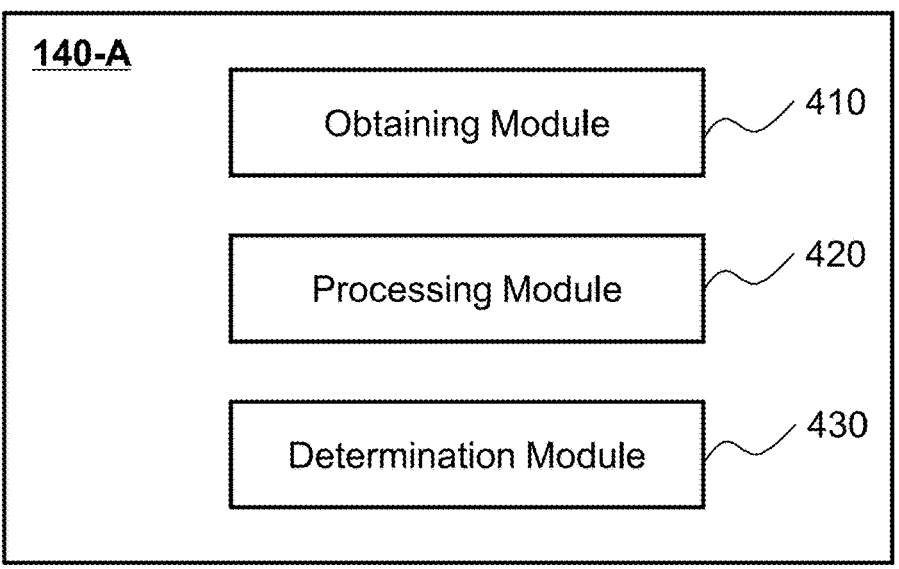
FIGS. 4A to 4C are block diagrams illustrating exemplary processing devices according to some embodiments of the present disclosure.
Figure 4B:
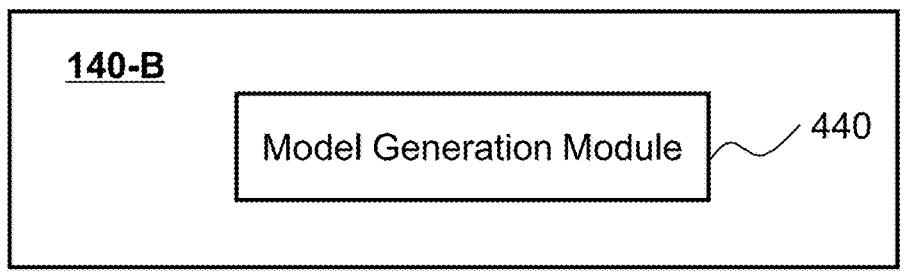
Figure 4C:
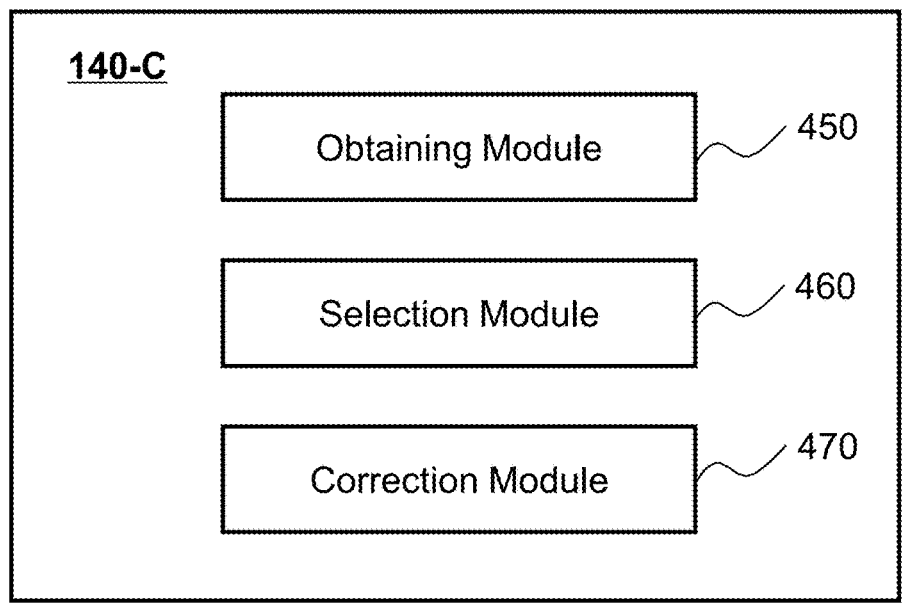

FIGS. 4A to 4C are a block diagrams illustrating exemplary processing devices 140-A, 140-B, and 140-C according to some embodiments of the present disclosure. In some embodiments, the processing device 140-A may be configured to process information and/or data to determine a set of training data. The processing device 140-B may be configured to train a preliminary neural network model using training data to generate a trained neural network model for scattering correction. The processing device 140-C may be configured to correct an image based on a trained neural network model for scattering correction. In some embodiments, the processing devices 140-A, 140-B, 140-C may respectively be implemented on a computing device 200 (e.g., the processor 210) illustrated in FIG. 2 or a CPU 340 as illustrated in FIG. 3. Merely by way of example, the processing devices 140-A and 140-B may respectively be implemented on a computing device 200, and the processing device 140-C may be implemented on a CPU 340 of a terminal device. Alternatively, at least two of the processing devices 140-A, 140-B, and 140-C may be implemented on a same computing device 200 or a same CPU 340. For example, the processing devices 140-A and the processing device 140-B may be implemented on a same computing device 200.

The processing device 140-A may include an obtaining module 410, a processing module 420, and a determination module 430.

The obtaining module 410 may be configured to obtain information related to the imaging system 100. The information may include scan data, image data (one or more images), or the like. In some embodiments, the information may further be used to determine a set of training data. For example, the obtaining module 410 may obtain a first image and a second image of the same subject. The second image may include less scattering noises than the first image. The first and second images may be used to determine a set of training data. In some embodiments, the obtaining module 410 may obtain the information related to the imaging system 100 from one or more components of the imaging system 100, such as the imaging device 110, a storage device (e.g., the storage device 150). Additionally or alternatively, the obtaining module 410 may obtain the information from an external source via the network 120.

The processing module 420 may process an image. The processing of the image may include an image rotation, an image flipping, an image normalization, an image enhancement, an image filtering, or the like, or any combination thereof. Merely by way of example, the processing module 420 may rotate the image and then normalize the rotated image. Details regarding the image processing may be found elsewhere in the present disclosure (e.g., step 530 of the process 500 and the relevant descriptions thereof).

The determination module 430 may determine a set of training data. For example, the determination module 430 may determine a set of training data based on a (processed) first image and a (processed) second image of the same subject. The (processed) second image may include less scattering noises than the (processed) first image. The set of training data may include input data and tag data. The tag data may also be referred to as reference data or label data. The determination module 430 may determine the input data based on the (processed) first image, and determine the tag data based on the (processed) second image. In some embodiments, the determination module 430 may respectively decompose the (processed) first image and the (processed) second image into a plurality of sets of decomposition data. The determination module 430 may also determine one or more sets of training data based on the sets of decomposition data. Details regarding the determination of a set training data may be found elsewhere in the present disclosure (e.g., step 550 of the process 500 and the relevant descriptions thereof).

The processing device 140-B may include a model generation module 440. The model generation module 440 may be configured to generate a trained neural network model for scattering correction by training a preliminary neural network model using training data. The training data may be acquired from one or more components in the imaging system 100 (e.g., the storage device 150, the processing device 140-A), and/or an external source. For example, the training data may include one or more sets training data generated by the processing device 140-A. In some embodiments, the model generation module 440 may input the training data into the preliminary neural network model to determine one or more model parameters. The model generation module 440 may further determine the trained neural network model for scattering correction based on the preliminary neural network model and the model parameter(s). Details regarding the generation of a trained neural network model may be found elsewhere in the present disclosure (e.g., step 560 of the process 500 and the process 700, and the relevant descriptions thereof).

The processing device 140-C may include an obtaining module 450, a selection module 460, and a correction module 470.

The obtaining module 450 may obtain information related to the imaging system 100. The information may include scan data, image data (one or more images), or the like. For example, the obtaining module 450 may obtain a target image to be corrected and one or more target imaging parameters under which the target image is generated. As another example, the obtaining module 450 may obtain one or more trained neural network models for scattering correction. In some embodiments, the obtaining module 450 may obtain the information from an external source and/or one or more components of the imaging system 100, such as a processing device 140 (e.g., the processing device 140-B), a storage device (e.g., the storage device 150).

The selection module 460 may select a target trained neural network model used to correct the target image among the plurality of trained neural network models for scattering correction. In some embodiments, the trained neural network models may correspond to a plurality of sets of imaging parameters. The selection module 460 may select the target trained neural network model based on differences between the target imaging parameters and each of the sets of imaging parameters. For example, the trained neural network model whose corresponding set of imaging parameters has the smallest difference with the target imaging parameters may be designated as the target trained neural network model.

The correction module 470 may correct an image based on a trained neural network model. For example, the correction module 470 may perform a scattering correction on the target image based on the target trained neural network model for scattering correction. In some embodiments, the target trained neural network model may be a trained multi-scale convolutional neural network model for scattering correction. The correction module 470 may decompose the target image into a plurality of decomposed target images, and correct each of the decomposed target images based on the multi-scale convolutional neural network model. The correction module 470 may also generate the corrected target image based on the plurality of corrected decomposed target images. Details regarding the correction of an image may be found elsewhere in the present disclosure (e.g., step 1350 of the process 1300 and the relevant descriptions thereof).

The modules in the processing devices 140A, 140B, and the 140C may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

In some embodiments, two or more of the modules of a processing device 140 (e.g., the processing device 140-A, the processing device 140-B, and/or the processing device 140C) may be combined into a single module, and any one of the modules may be divided into two or more units. For example, the model generation module 440 may be divided into two units. The first unit may be configured to acquire a preliminary neural network model, and the second unit may be configured to determine one or more model parameters and determine a trained neural network model. In some embodiments, a processing device 140 (the processing device 140-A, the processing device 140-B, and/or the processing device 140C) may include one or more additional modules. For example, the processing device 140A may include a storage module (not shown) configured to store data. In some embodiments, any two or more of the processing devices 140-A, 140-B, and 140-C may be integrated to a single processing device 140 to perform the functions thereof. Merely by way of example, the processing device 140-A and the processing device 140-B may be integrated into a processing device 140. The integrated processing device 140 may determine one or more sets of training data, and train a preliminary neural network model using the one or more determined sets of training data and other sets of training data (if any).

Figure 5:
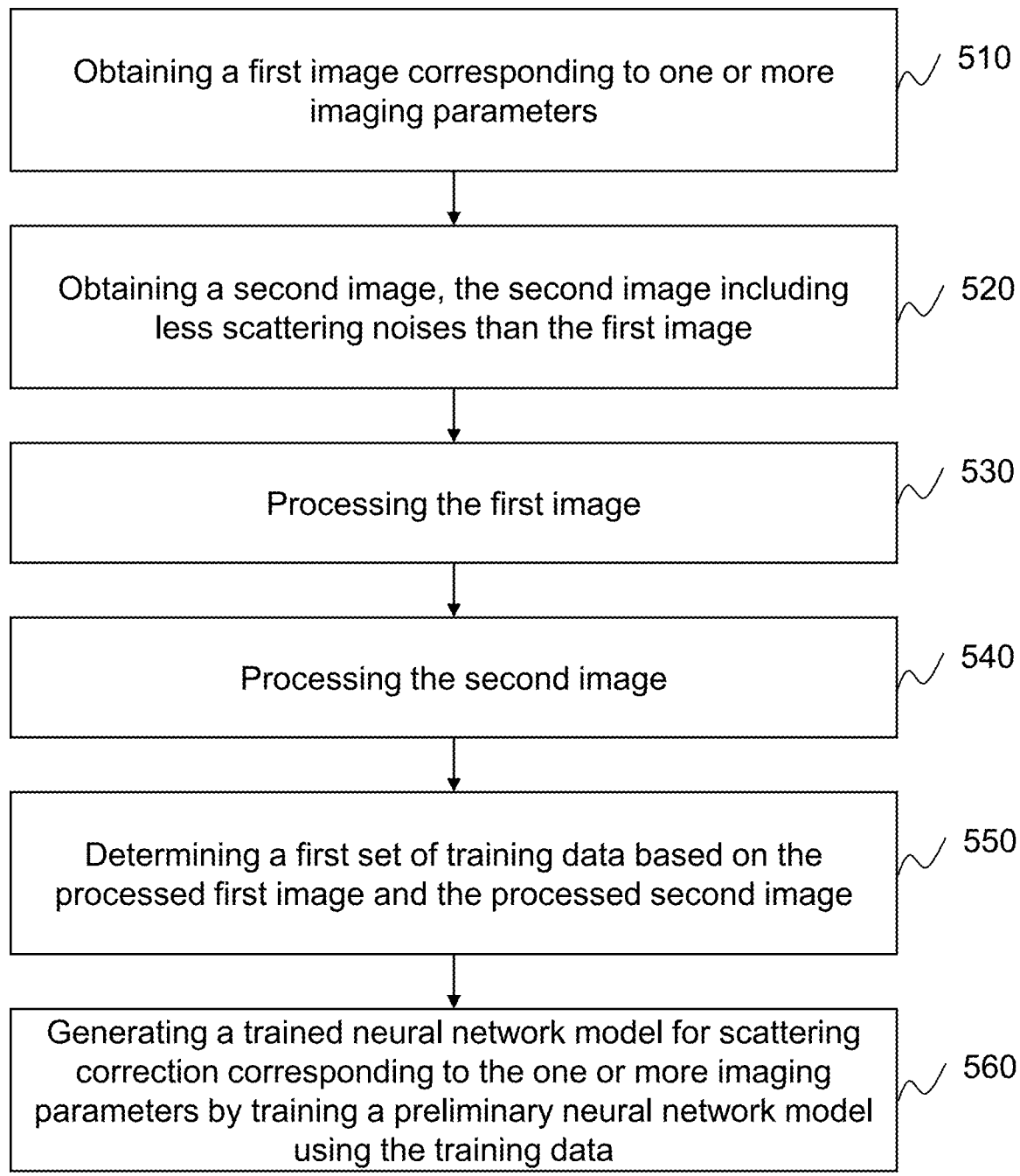
FIG. 5 is a flowchart illustrating an exemplary process for generating a trained neural network model for scattering correction according to some embodiments of the present disclosure.

FIG. 5 is a flowchart illustrating an exemplary process for generating a trained neural network model for scattering correction according to some embodiments of the present disclosure. The process 500 may be implemented in the imaging system 100 illustrated in FIG. 1. For example, the process 500 may be stored in the storage device 150 and/or the storage 220 in the form of instructions (e.g., an application), and invoked and/or executed by the processing device 140 (e.g., the processor 210 illustrated in FIG. 2, or one or more modules in the processing device 140-A illustrated in FIG. 4A, and/or in the processing device 140-B illustrated in FIG. 4B). The operations of the illustrated process presented below are intended to be illustrative. In some embodiments, the process 500 may be accomplished with one or more additional operations not described, and/or without one or more of the operations discussed. Additionally, the order in which the operations of the process 500 as illustrated in FIG. 5 and described below is not intended to be limiting.

In 510, the obtaining module 410 may obtain a first image corresponding to one or more imaging parameters. In some embodiments, "obtaining a first image" may refer to obtaining the first image and/or image data related to the first image. The image date related to the first image may include, for example, pixel values of one or more pixels or voxel values of one or more voxels in the first image.

In some embodiments, the first image may be simulated under the one or more image parameters by a Monte-Carlo technique. Alternatively, the first image may be generated according to first scan data acquired by an imaging device (e.g., the imaging device 110) under one or more imaging parameters. In some embodiments, the one or more imaging parameters may include a tube voltage, a tube current, a scanning time, an irradiation dose, a slice thickness of scanning, or the like, or any combination thereof. In some embodiments, the one or more imaging parameters may be determined based on a scanning plan. Different scanning plans may include different imaging parameters depending on different diagnostic needs.

The imaging device 110 may perform a first scan on a subject according to the one or more imaging parameters to collect the first scan data. The subject may be a biological subject (e.g., a human, an animal) or a non-biological subject (e.g., a phantom). In some embodiments, the imaging device 110 may be configured without a grid during the first scan. The grid may be configured to reduce or eliminate radiation scattering. The first image may be generated according to the first scan data, which may include scattering noises. In some embodiments, the obtaining module 410 may obtain the first image from one or more components of the imaging system 100, such as the imaging device 110, a storage device (e.g., the storage device 150). Alternatively, the obtaining module 410 may obtain the first image from an external source via the network 120.

In 520, the obtaining module 410 may obtain a second image. The second image may include less scattering noises than the first image. In some embodiments, "obtaining a second image" may refer to obtaining the second image and/or image data related to the second image. The image date related to the second image may include, for example, pixel values of one or more pixels or voxel values of one or more voxels in the second image In some embodiments, the second image may be generated according to second scan data acquired by the imaging device 110. For example, the imaging device 110 may be configured with the grid and perform a second scan on the subject under the same imaging parameter(s) as the first scan to obtain the second scan data. The grid may reduce or eliminate radiation scattering, and the second image may include less scattering noises than the first image. As another example, the second image may be generated based on the first image by removing at least some of the scattering noises of the first image. For example, a scattering correction may be performed on the first image to generate the second image. Exemplary scattering correction techniques may include an image smoothing technique, an image enhancement technique, a Monte Carlo simulation technique, a single scatter simulation technique, a dual energy-window technique, a tail fitting technique, or the like, or any combination thereof. As yet another example, an image may be generated according to the second scan data. The second image may be determined based on the image by removing at least some of the scattering noises of the image.

In some embodiments, the first and the second images may be simulated images generated according to a Monte-Carlo technique. The first image may be simulated to include more scattering noises than the second image. Merely by way of example, the first image may be an image including scattering noises simulated by the Monte-Carlo technique. The second image may be an image without scattering noises simulated by the Monte-Carlo technique. The simulations of the first and second images may be performed under the same one or more imaging parameters as described in connection with operation 510.

In some embodiments, the obtaining module 410 may obtain the second image from one or more components of the imaging system 100, such as the imaging device 110, a storage device (e.g., the storage device 150). Alternatively, the obtaining module 410 may obtain the second image from an external source via the network 120.

In 530, the processing module 420 may process the first image. The processing of the first image may include an image rotation, an image flipping, an image normalization, an image enhancement, an image filtering, or the like, or any combination thereof. For example, the processing module 420 may flip the first image horizontally, vertically, or in any other direction. Alternatively or additionally, the processing module 420 may rotate the first image by an angel. The first image may be rotated clockwise or counterclockwise. The angle may be any value between 0 and 360°. In some embodiments, the processing module 420 may normalize the first image with respect to its range of pixel values according to a normalization technique. Exemplary normalization techniques may include a min-max normalization algorithm, a Z-score standardization technique, a linear normalization technique, etc. In some embodiments, the pixel value of each pixel in the first image may be normalized according to Equation (1) as below:

$$N_i = \frac{P_i - I_{min}}{I_{max} - I_{min}}, \quad (1)$$

where $I_{max}$ refers to the maximum pixel value of the first image; $I_{min}$ refers to the minimum pixel value of the first image; i refers to a pixel in the first image; $P_i$ refers to the pixel value of the pixel i; and $N_i$ refers to a normalized pixel value of the pixel i.

Alternatively, the pixel value of each pixel in the first image may be normalized according to Equation (2) as below:

$$N_i = \frac{P_i - I_a}{nI_v}, \quad (2)$$

where $I_a$ refers to an average pixel value of the first image; $I_v$ refers to a variance of pixel values of the first image; n refers to a coefficient; i refers to a pixel in the first image; $P_i$ refers to the pixel value of the pixel i; and $N_i$ refers to the normalized value of the pixel i. The coefficient n may have any positive value. For example, n may be 3.

In some embodiments, the processing module 420 may perform a plurality of processing operations on the first image. For example, the processing module 420 may transform the first image by flipping and/or rotating the first image, and then normalize the transformed first image. As another example, the processing module 420 may normalize the first image, and then transform the normalized first image by flipping and/or rotating the normalized first image. In some embodiments, the processing module 420 may flip the first image in different directions, and/or rotate the first image by different angles to generate a plurality of transformed first images. Additionally or alternatively, the processing module 420 may normalize the transformed first images.

In 540, the processing module 420 may process the second image. The processing of the second image may include an image rotation, an image flipping, an image normalization, an image enhancement, an image filtering, or the like, or any combination thereof. The second image may be processed in the same or substantially same manner as the first image. For example, the second image may be rotated by the same angle as the first image, and then be normalized by the same way as the first image. Details regarding the image processing (e.g., the image rotation, the image normalization) may be found elsewhere in the present disclosure (e.g., step 530 and the relevant descriptions thereof).

In 550, the determination module 430 may determine a first set of training data based on the processed first image and the processed second image.

In some embodiments, the first set of training data may include input data and tag data. The input data may be determined based on the processed first image, and the tag data may be determined based on the processed second image. For example, the determination module 430 may select a first sub-area from the processed first image, and designate the image data corresponding to the first sub-area (e.g., the pixel values of the pixel in the first sub-area) as the input data. The determination module 430 may select a second sub-area corresponding to the first sub-area from the processed second image. The determination module 430 may also designate the image data corresponding to the second sub-area as the tag data. The second sub-area corresponding to the first sub-area may have the same position in the processed second image as that of the first sub-area in the processed first image.

In some embodiments, the first sub-area may be selected in a random way or according to a sampling window. The sampling window may have any size and be located at any position in the first image. In some embodiments, the number of pixels in a side of the sampling window may range from 40 to 100. The size of the sampling window may range from 40×40 to 100×100. Merely by way of example, the size of the first sub-area may be 50×50, 70×70, or the like. After the first sub-area is selected, the determination module 430 may select the second sub-area locating at the same position as the first sub-area from the second image.

In some embodiments, steps 530 and 540 may be omitted. The determination module 430 may determine the first set of training data based on the first image and the second image. The first set of training data may include input data and tag data. The input data may be determined based on the first image, and the tag data may be determined based on the second image. The determination of the input data and the tag data based on the first and second images may be similar to that based on the processed first and processed second images, and the descriptions thereof are not repeated.

In some embodiments, the determination module 430 may decompose the (processed) first image into a plurality of sets of first decomposition data, and decompose the (processed) second image into a plurality of sets of second decomposition data. The determination module 430 may also determine the first set of training data based on the sets of first and second decomposition data. In some embodiments, the first set of training data determined based on the sets of first and second decomposition data may correspond to a specific frequency band. Details regarding the determination of the first set of training data based on the first and second decomposition data may be found elsewhere in the present disclosure (e.g., FIG. 6, and the relevant descriptions thereof).

In 560, the model generation module 440 may generate a trained neural network model for scattering correction corresponding to the one or more imaging parameters by training a preliminary neural network model using training data. The training data may include at least one of the first set of training data.

In some embodiments, the training data may include a plurality of first sets of training data. Different first sets of training data may be generated in the same way or different ways. For example, in 530, the processing module 420 may process (e.g., rotate, flip, and/or normalize) the first image to generate a plurality of processed first images. In 540, the processing module 420 may process (e.g., rotate, flip, and/or normalize) the second image to generate a plurality of processed second images. The determination module 430 may determine a plurality of first sets of training data by repeating step 550 for each processed first image and the corresponding processed second image. As another example, in step 550, the determination module 430 may select a plurality of first sub-areas and corresponding second sub-areas from the first image and second image respectively. The determination module 430 may further determine a plurality of first sets of training data based on the first sub-areas and the second sub-areas. As yet another example, steps 510 to 550 may be performed on a plurality of first images and a plurality of second images to generate a plurality of first sets of training data.

In some embodiments, the training data may include one or more first sets of training data that have a specific characteristic. For example, the training data may include one or more first sets of training data that correspond to a frequency band. The trained neural network model for scattering correction generated based on the training data may be used to correct an image (or a portion thereof) that corresponds to the frequency band. In some embodiments, the training data may further include one or more sets of training data suitable for training a neural network model for scattering correction. The sets of training data may be generated in a similar or different way as the first set of training data.

In some embodiments, the preliminary neural network model may include a convolutional neural network model, a perceptron neural network model, a deep trust network model, a stack self-coding network model, a recurrent neural network model, or the like, or any combination thereof. The preliminary neural network model may include one or more preliminary parameters. The model generation module 440 may input the training data into the preliminary neural network model to adjust the preliminary parameters. The adjusted parameters may be referred to as model parameters. The trained neural network model for scattering correction may be determined based on the model parameters and the preliminary neural network model. Details regarding the generation of a trained neural network model for scattering correction may be found elsewhere of the present disclosure (e.g., FIG. 7, and the relevant descriptions thereof).

It should be noted that the above description of the process 500 is provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. For example, steps 530 and 540 may be omitted. The determination module 430 may determine the first set training data based on the first image and the second image. As another example, step 530 may be performed before step 540, or steps 530 and 540 may be performed simultaneously. As yet another example, step 560 may be omitted. In some embodiments, the process 500 may repeatedly be performed to generate a plurality of trained neural network model for scattering correction corresponding to a plurality of sets of imaging parameters. Different trained neural network models corresponding to different sets of imaging parameters may be used to correct images acquired under different sets of imaging parameters (will be described in FIG. 13).

Figure 6:
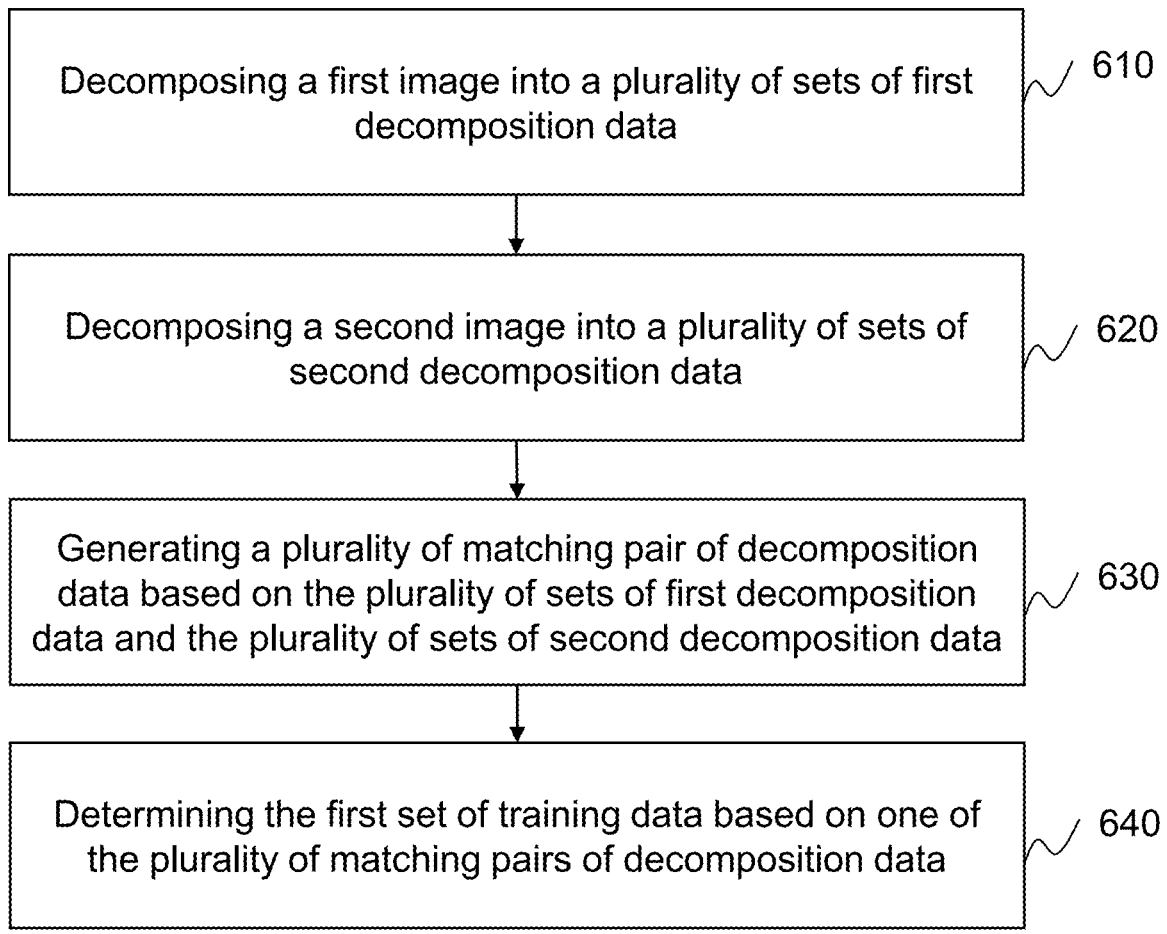
FIG. 6 is a flowchart illustrating an exemplary process for determining a first set of training data according to some embodiments of the present disclosure.

FIG. 6 is a flowchart illustrating an exemplary process for determining a first set of training data according to some embodiments of the present disclosure. The process 600 may be implemented in the imaging system 100 illustrated in FIG. 1. For example, the process 600 may be stored in the storage device 150 and/or the storage 220 in the form of instructions (e.g., an application), and invoked and/or executed by the processing device 140 (e.g., the processor 210 illustrated in FIG. 2, or one or more modules in processing device 140-A illustrated in FIG. 4A). The operations of the illustrated process presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting. In some embodiments, the steps 530 and 540 of process 500 may be omitted. The step 550 of the process 500 may be performed according to the process 600.

In 610, the determination module 430 may decompose the first image into a plurality of sets of first decomposition data. The number of the sets of first decomposition data may be any positive value, for example, 4, 7, or 10. In some embodiments, the number of the sets of first decomposition data may range from 4 to 8. In some embodiments, the sets of first decomposition data may include a plurality of first decomposed images.

In some embodiments, the first image may be decomposed according to a frequency of at least one of the first image or image data (e.g., pixel values or voxel values) related to the first image. The sets of first decomposition data may correspond to a plurality of frequency bands. In some embodiments, the determination module 430 may decompose the first image according to an image decomposition technique. Exemplary image decomposition techniques may include a wavelet decomposition technique, a Laplacian decomposition technique, a Gaussian decomposition technique, a singular value decomposition technique, or the like, or any combination thereof. Merely by way of example, the first image may be decomposed into seven sets of first decomposition data corresponding to seven frequency bands according to the Laplacian decomposition technique (which will be described in detail in connection with FIG. 12).

In 620, the processing engine 130 may decompose the second image into a plurality of sets of second decomposition data. The second image may be decomposed according to a frequency of at least one of the second image or image data (e.g., pixel values or voxel values) related to the second image. The second image may be decomposed in the same or substantially same manner as the first image. The sets of second decomposition data may correspond to the same or substantially same frequency bands as the sets of first decomposition data. The number of the sets of second decomposition data may be equal to the number of sets of the first decomposition data. In some embodiments, the sets of second decomposition data may include a plurality of second decomposed images.

In 630, the determination module 430 may generate a plurality of matching pairs of decomposition data based on the sets of first and second decomposition data. Each of the matching pairs may include a set of first decomposition data and a corresponding set of second decomposition data. In some embodiments, as described in connection with steps 610 and 620, the sets of first and second decomposition data may correspond to a plurality of frequency bands respectively. The set of first decomposition data and its corresponding set of second decomposition data may correspond to the same frequency band.

In 640, the determination module 430 may determine the first set of training data based on one of the matching pairs of decomposition data. The first set of training data may include input data and tag data as described in connection with step 550 of the process 500. For a matching pair of decomposition data, the input data may be determined based on the set of first decomposition data (e.g., a first decomposed image), and the tag data may be determined based on the corresponding set of second decomposition data (e.g., a second decomposed image). The determination of the input data based on the set of first decomposition data may be similar to that based on the (processed) first image. The determination of the tag data based on the set of second decomposition data may be similar to that based on the (processed) second image. For example, the determination module 430 may select a third sub-area from the set of first decomposition data (e.g., a first decomposed image). The determination module 430 may also designate the image data corresponding to the third sub-area (e.g., the pixel values of the pixel in the third sub-area) as the input data. The determination module 430 may further select a fourth sub-area corresponding to the third sub-area from the set of second decomposition data (e.g., a second decomposed image) and designate the image data corresponding to the fourth sub-area as the tag data. The fourth sub-area corresponding to the third sub-area may have the same position in the set of second decomposition data as that of the third sub-area in the set of first decomposition data. Details regarding the determination of input data and tag data may be found elsewhere in the present disclosure (e.g., step 550 of the process 500, and the relevant descriptions thereof).

In some embodiments, the sets of first and second decomposition data of a matching pair may correspond to a frequency band. The first set of training data generated based on the matching pair may be used to generate a trained neural network model corresponding to the frequency band by performing step 560. The trained neural network model corresponding to the frequency band may further be used to correct an image (or a portion thereof) that corresponds to the frequency band (which will be described in detail in connection with FIG. 13).

In some embodiments, for each of the matching pairs of decomposition data, the determination module 430 may determine a first set of training data. Accordingly, a plurality of first sets of training data corresponding to different frequency bands may be determined in 640. The first sets of training data may further be used to generate a plurality of trained neural network models for scattering correction corresponding to the different frequency bands. Alternatively, the first sets of training data may be used to generate a trained multi-scale convolutional neural network model for scattering correction. Details regarding the trained multi-scale convolutional neural network model may be found elsewhere in the present disclosure (e.g., FIGS. 12 and 14, and the relevant descriptions thereof). In some embodiments, a process similar to the process 600 may be performed on a processed first image and a processed second image to achieve step 550 of the process 500. For example, the determination module 430 may respectively decompose the processed first image and the processed second image into sets of decomposition data. The determination module 430 may further determine a plurality of matching pairs of decomposition data based on the sets of decomposition data, and determine the first set of training data accordingly.

Figure 7:
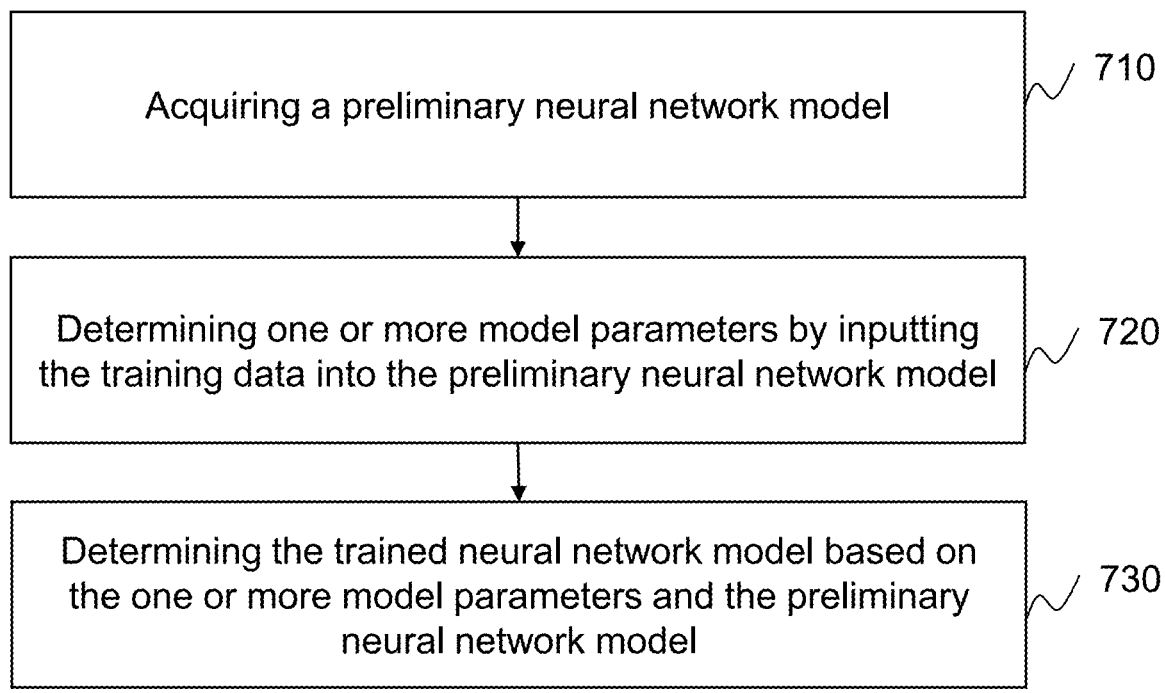
FIG. 7 is a flowchart illustrating an exemplary process for generating a trained neural network model for scattering correction according to some embodiments of the present disclosure.

FIG. 7 is a flowchart illustrating an exemplary process for generating a trained neural network model for scattering correction according to some embodiments of the present disclosure. The process 700 may be implemented in the imaging system 100 illustrated in FIG. 1. For example, the process 700 may be stored in the storage device 150 and/or the storage 220 in the form of instructions (e.g., an application), and invoked and/or executed by the processing device 140 (e.g., the processor 210 illustrated in FIG. 2, or one or more modules in the processing device 140-B illustrated in FIG. 4B). The operations of the illustrated process presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting. In some embodiments, the process 700 may be an embodiment of step 560 of the process 500.

In 710, the model generation module 440 may acquire a preliminary neural network model. The preliminary neural network model may include one or more preliminary parameters. The one or more preliminary parameters may be adjusted during the training process of the preliminary neural network model.

In some embodiments, exemplary preliminary neural network models may include a convolutional neural network model (e.g., a multi-scale convolutional neural network model, a super-resolution convolutional neural network model, a denoising convolutional neural network model), a perceptron neural network model, a deep trust network model, a stack self-coding network model, a recurrent neural network model (e.g., a long short term memory (LSTM) neural network model, a hierarchical recurrent neural network model, a bi-direction recurrent neural network model, a second-order recurrent neural network model, a fully recurrent network model, an echo state network model, a multiple timescales recurrent neural network (MTRNN) model), or the like, or any combination thereof. In some embodiments, the preliminary neural network model may be a convolutional neural network model that includes a convolution layer, an activation layer, and a cost layer. Details regarding the convolutional neural network model may be found elsewhere in the present disclosure (e.g., FIGS. 9 to 11, and the relevant descriptions thereof).

In 720, the model generation module 440 may determine one or more model parameters by inputting the training data into the preliminary neural network model. The training data may correspond to a set of one or more imaging parameters under which images (e.g., the first image, the second image described in FIG. 5) may be generated. The training data may include input data and tag data as described in connection with steps 550 and 640.

In some embodiments, the input data may be inputted into the preliminary neural network model to generate an actual output. The tag data may be considered as a desired output. The model generation module 440 may compare the actual output with the desired output to determine a loss function. The loss function may measure a difference between the actual output and the desired output (i.e., the tag data). During the training of the preliminary neural network model, the model generation module 440 may adjust the one or more preliminary parameters to minimize the loss function. In some embodiments, the loss function and the preliminary parameters may be updated iteratively in order to obtain a minimized loss function. The iteration to minimize the loss function may be terminated until a termination condition is satisfied. An exemplary termination condition is that an updated loss function with the updated parameters obtained in an iteration is less than a predetermined threshold. The predetermined threshold may be set manually or determined based on various factors including, such as the accuracy of the trained neural network model, etc. Other exemplary termination conditions include that a certain iteration count of iterations are performed, that the loss function converges such that the differences of the values of the updated loss function obtained in consecutive iterations are within a threshold, etc.

After the loss function is minimized, the one or more newly adjusted preliminary parameters may be designated as the one or more model parameters of the trained neural network model.

In some embodiments, the one or more model parameters may include a relationship between the input data and the tag data. In some embodiments, the relationship between the input data and the tag data may be a mapping function. Details regarding the determination of the relationship between the input data and the tag data may be found elsewhere in the present disclosure (e.g., FIG. 8, and the relevant descriptions thereof).

In 730, the model generation module 440 may determine the trained neural network model based on the one or more model parameters and the preliminary neural network model. For example, the one or more model parameters may be combined with the preliminary neural network model to generate the trained neural network model. The trained neural network model may be used for scattering correction. In some embodiments, the training data may correspond to one or more imaging parameters. The trained neural network model may be used to correct an image generated under the same or substantially same imaging parameters as the training data.

In some embodiments, the preliminary neural network model may be a multi-scale convolutional neural network model that includes a plurality of sub-convolutional neural network models. The training data of the multi-scale convolutional neural network model may include a plurality of sets of training data that correspond to a plurality of frequency bands. Steps 720 and 730 may be performed for each sub-convolutional neural network model based on a set of training data to generate a trained sub-convolutional neural network model. A trained multi-scale convolutional neural network model (e.g., the trained multi-scale convolutional neural network model 1210) may further be determined by combining the trained sub-convolutional neural network models. Details regarding the training of a multi-scale convolutional neural network model may be found elsewhere in the present disclosure (e.g., FIG. 12 and the relevant descriptions thereof).

Figure 8:
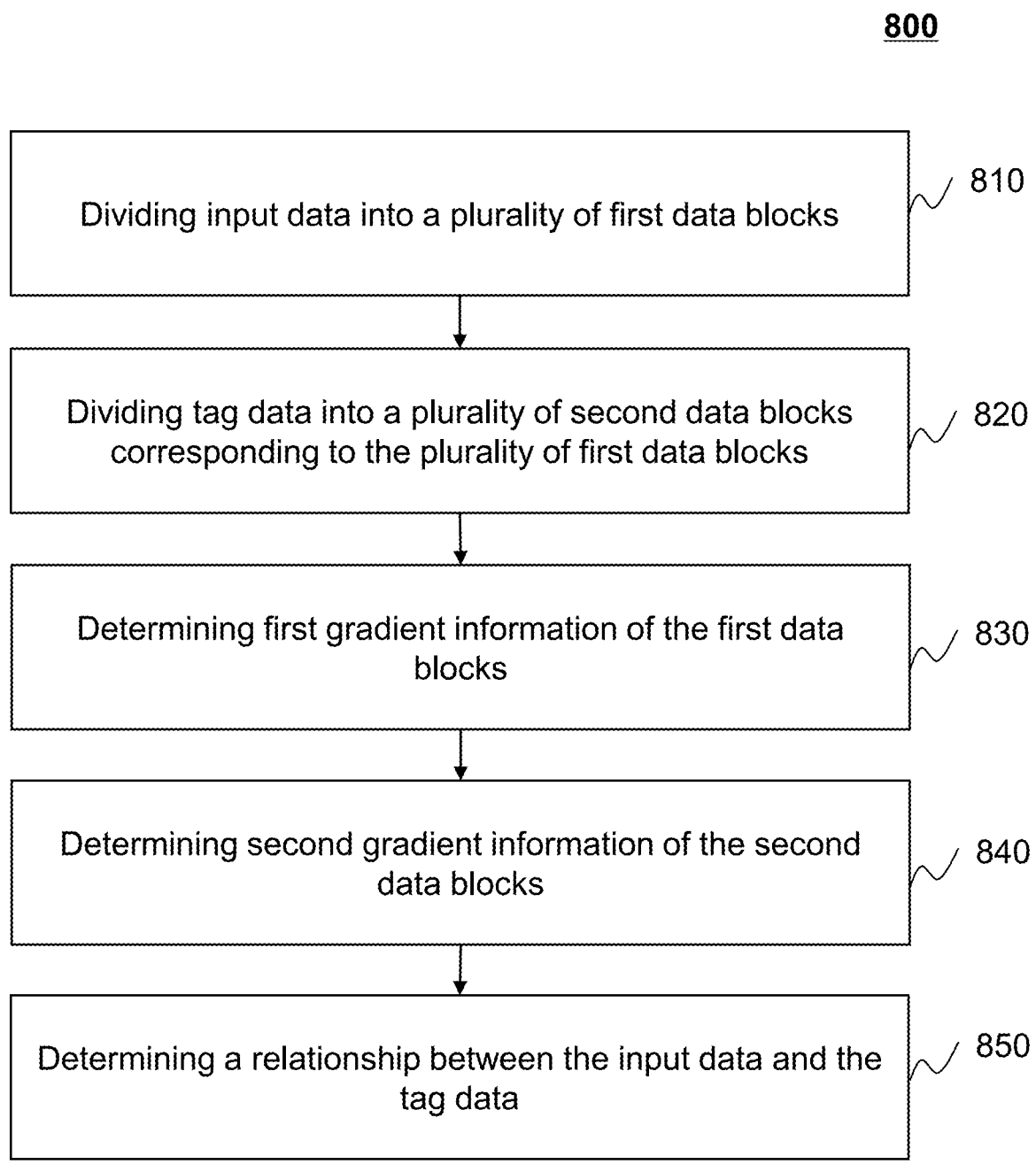
FIG. 8 is a flowchart illustrating an exemplary process for determine a relationship between input data and tag data according to some embodiments of the present disclosure.

FIG. 8 is a flowchart illustrating an exemplary process for determining a relationship between input data and tag data according to some embodiments of the present disclosure. The process 800 may be implemented in the imaging system 100 illustrated in FIG. 1. For example, the process 800 may be stored in the storage device 150 and/or the storage 220 in the form of instructions (e.g., an application), and invoked and/or executed by the processing device 140 (e.g., the processor 210 illustrated in FIG. 2, or one or more modules in the processing device 140-B illustrated in FIG. 4B). The operations of the illustrated process presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting. In some embodiments, the process 800 may be an embodiment of step 720 of the process 7000.

In 810, the model generation module 440 may divide input data into a plurality of first data blocks. The input data may be determined based on a (processed) first image and/or a first decomposed image as described elsewhere in this disclosure (e.g., steps 550 and 640, and the relevant descriptions). The input data may include a plurality of pixel values of pixels in the (processed) first image and/or the first decomposed image. In some embodiments, the input data may be evenly divided or unevenly divided. The sizes of different first data blocks may be the same or different.

In 820, the model generation module 440 may divide tag data into a plurality of second data blocks corresponding to the plurality of first data blocks. The tag data may be determined based on a (processed) second image and/or a second decomposed image as described elsewhere in this disclosure (e.g., step 550 of the process 500 and step 640 of the process 600, and the relevant descriptions). The tag data may include a plurality of pixel values of pixels in the (processed) second image and/or the second decomposed image. The tag data may be divided in the same or substantially same manner as the input data. The number of the second data blocks may be equal to the number of the first data blocks. The size of a second data block may be equal to the corresponding first data block.

In 830, the model generation module 440 may determine first gradient information (also referred to as a first gradient structure) of the first data blocks. The first gradient information of the first data blocks may include first gradient information of each first data block. The first gradient information of a first data block may include X-direction gradient information and Y-direction gradient information of each pixel in the first data block. Merely by way of example, for a pixel in a first data block, the model generation module 440 may respectively determine X-direction gradient information and Y-direction gradient information of the pixel according to Equation (3) and Equation (4) as below:

$$G_X(i, j) = \begin{cases} 0, & i = 0 \\ I(i, j) - I(i-1, j), & i \geq 1 \end{cases} \quad (3)$$

$$G_Y(i, j) = \begin{cases} 0, & j = 0 \\ I(i, j) - I(i, j-1), & j \geq 1 \end{cases} \quad (4)$$

wherein i refers to an abscissa of the pixel; j refers to an ordinate of the pixel; I refers to the pixel value (e.g., the grey value) of the pixel; $G_X$ refers to the X-direction gradient information of the pixel; and $G_Y$ refers to the Y-direction gradient information of the pixel. The i and j may both be positive.

The first gradient information for different pixels may be the same or different. For example, the first gradient information of a pixel in a first data block located at the edge of the (processed) first image may be greater than that of a pixel in the first data block located at the center of the (processed) first image.

In 840, the model generation module 440 may determine second gradient information (also referred to as a second gradient structure) of the second data blocks. The second gradient information of the first data blocks may include second gradient information of each second data block. The second gradient information of a second data block may include X-direction gradient information and Y-direction gradient information of each pixel in the second data block. The second gradient information of the second data blocks may be determined in the same or substantially same manner as the first gradient information.

In 850, the model generation module 440 may determine a relationship between the input data and the tag data. The relationship between the input data and the tag data may refer to a relationship between the first gradient information of the first data blocks and the second gradient information of the second data blocks. In some embodiments, the relationship may be expressed by a map function between the first gradient information and the second gradient information.

In some embodiments, the relationship between the input data and the tag data may be used to transform the first gradient information of the first data blocks. The transformed first gradient information may be regarded as an actual output generated by a (trained) neural network model with the input data as the input to the (trained) neural network model. In some embodiments, the transformed first gradient information may further be transformed into image data. Exemplary techniques to transform gradient information into image data may be found in, for example, a literature entitled "DIRECT ANALYTICAL METHODS FOR SOLVING POISSON EQUATIONS IN COMPUTER VISION PROBLEMS" published on "IEEE Transactions on Pattern Analysis and Machine Intelligence" on 1990, the contents of which are hereby incorporated by reference.

In some embodiments, the input data and the tag data may respectively be determined based on a first and second decomposed image that corresponds to a frequency band as described in connection with step 640. The relationship between the input data and the tag data may be regarded as a relationship between the first decomposed image and the second decomposed image.

In some embodiments, the model generation module 440 may determine gradient information (e.g., X-direction gradient information and/or Y-direction gradient information) of each pixel in the input data and the tag data. The model generation module 440 may divide the input data into the first data blocks, and divide the tag data into the second data blocks. The gradient information of the pixel(s) in a first data block may be designated as first gradient information of the first data block. The gradient information of the pixel(s) in a second data block may be designated as second gradient information of the second data block.

Figure 9A:
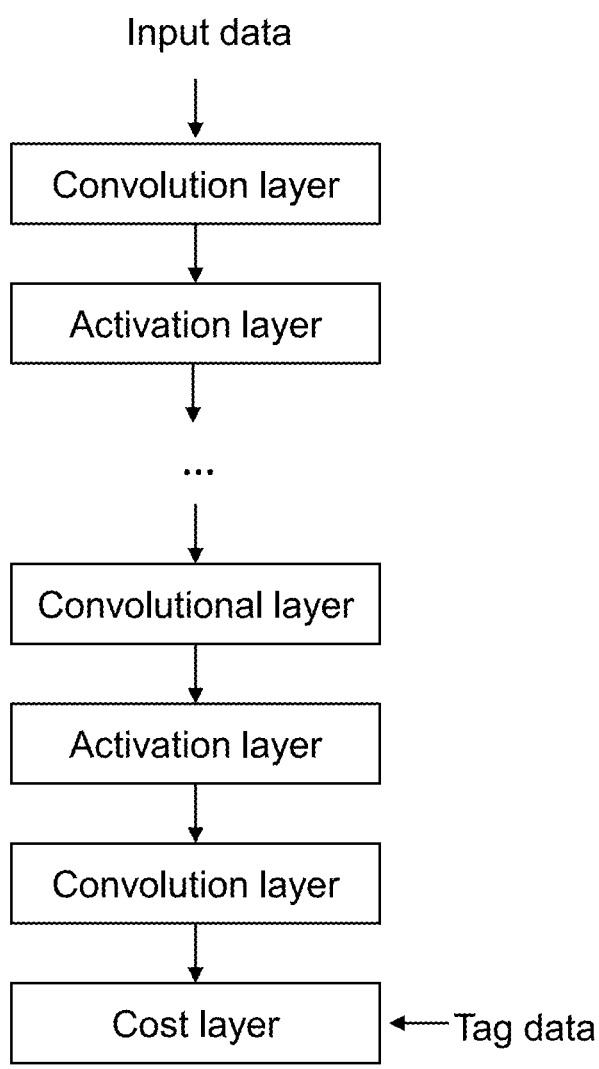
FIGS. 9A and 9B show exemplary convolutional neural network models according to some embodiments of the present disclosure.
Figure 9B:
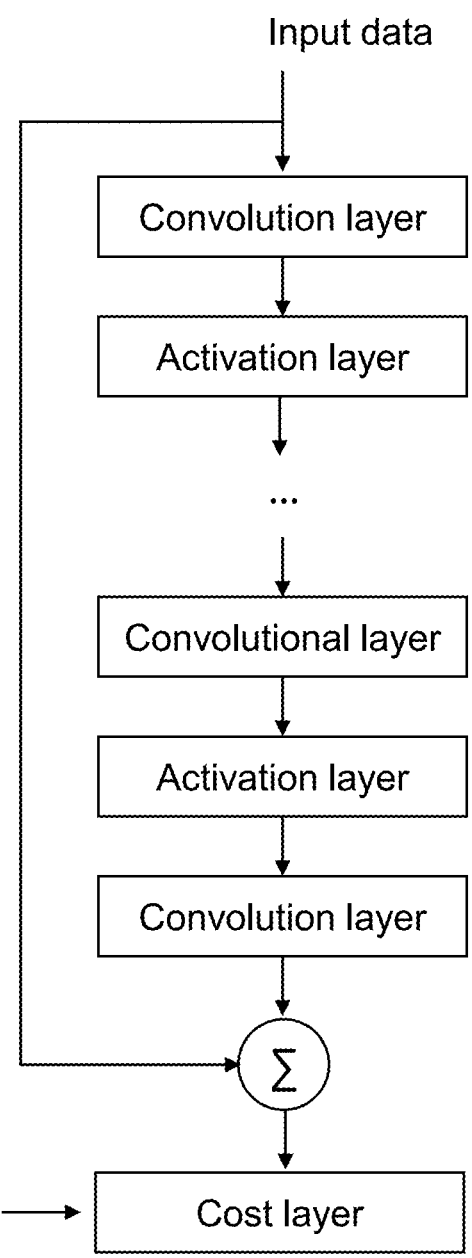

FIGS. 9A and 9B show two exemplary convolutional neural network models 900A and 900B according to some embodiments of the present disclosure. In some embodiments, the convolutional neural network models 900A and 900B may be embodiments of a preliminary neural network model. The convolutional neural network models 900A and/or 900B may be trained to generate a trained neural network model for scattering correction as described elsewhere in this disclosure (e.g., FIGS. 5 and 7, and the relevant descriptions).

As shown in FIGS. 9A and 9B, the convolutional neural network models 900A and 900B may respectively include one or more convolutional layers, one or more activation layers, and a cost layer. Each convolutional layer other than the last convolutional layer may be followed by an activation layer. The last convolutional layer may be followed by the cost layer. In some embodiments, the number of the convolutional layers may be within a range of 5 to 13. For example, the convolutional neural network model 900A may include five convolutional layers, four activation layers, and one cost layer. As another example, the convolutional neural network model 900A may include nine convolutional layers, eight activation layers, and one cost layer. The kernel size of a convolutional layer may be within a range of 3*3 to 11*11. For example, the kernel size of a convolutional layer may be 3*3. Different convolution layers may have the same kernel size or different kernel sizes. It should be noted that the above-described structure of the convolutional neural network model 900A and/or 900B is merely provided for the purposes of illustration, and not intended to limit the scope of the present disclosure. The convolutional neural network model 900A and/or 900B may include any number of convolutional layers and activation layers. The kernel size of a convolutional layer may be any positive value.

During a training process of the convolutional neural network model 900A or 900B, the input data (e.g., the one or more first data blocks, the first gradient information described in FIG. 8) may be inputted into the first convolutional layer and the first activation layer, and a plurality of feature maps (or feature data) may be generated. For the convolutional layer(s) other than the first or last ones, the input may include a plurality of feature maps (or feature data) generated by the previous convolutional layer, and the output may include a plurality of feature maps (or feature data. For the last convolutional layer, the input may include a plurality of feature images (or feature data) generated by the previous convolution layer, and the output may include a residual image (or residual data). In some embodiments, 64 feature maps may be generated by the first convolutional layer. The number of feature maps inputted in and/or outputted by a convolutional layer may be 64. In some embodiments, a feature map may be also referred to as a convolutional image.

An activation layer may be represented by an activation function. Exemplary activation functions may include a rectified linear unit (ReLU), an exponential linear unit (ELU), a leaky ReLU, a parameterized ReLU (PReLU), a randomized ReLU (RReLU), a noisy ReLU, or the like, or any combination thereof. Different activation layers may adopt the same activation function or different activation functions.

The cost layer may be represented by a loss function that measures a similarity (or a difference) between the tag data and an actual output. The actual output may be generated by inputting the input data into the convolutional neural network model 900A or 900B. The actual output may also be referred to as reconstructed data (will be described in FIG. 10). In some embodiments, when the loss function is equal to or less than a threshold, the training may be terminated since the similarity between the actual output and the tag data reaches a desired level. Exemplary loss functions may include a mean-square error (MSE) function, a mean absolute percent error (MAPE), a root mean square error (RMSE), a cross entropy function, a norm, etc. The norm may be, for example, a 1-norm, a weighted 1-norm, or a weighted 2-norm of the actual output and the tag data. Merely by way of example, the loss function may be the MSE function expressed by Equation (5) as below:

$$\text{Loss} = \frac{1}{N}\sum_{i=1}^{N} \|R(X_i) - c_i\|^2, \qquad (5)$$

wherein $X_i$ refers to the $i^{th}$ first data block of the input data; $R(X_i)$ refers to an actual output of the $i^{th}$ first data block $X_i$ based on the convolutional neural network model 900A or 900B; $c_i$ refers to the $i^{th}$ second data block of the tag data; and N refers to the number of the first or second data blocks.

In some embodiments, as illustrated in FIG. 9A, the output of the last convolution layer may be inputted into the cost layer to determine the cost function. As illustrated in FIG. 9B, the output of the last convolution layer may be added with the input data, and the sum of the input data and the output of the last convolution layer may be inputted into the cost layer to determine the cost function.

Figure 10:
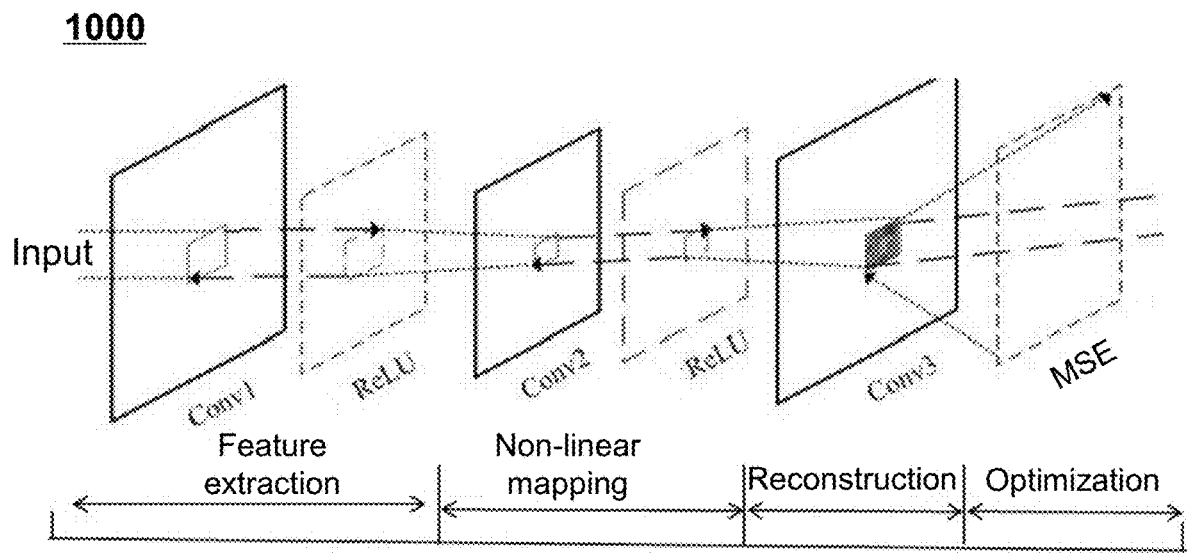
FIG. 10 shows a schematic diagram of an exemplary process for training a convolutional neural network model according to some embodiments of the present disclosure.

FIG. 10 shows a schematic diagram of an exemplary process for training a convolutional neural network model according to some embodiments of the present disclosure. The convolutional neural network model 1000 to be trained may be a super-resolution convolutional neural network (SRCNN) model. As illustrated in FIG. 10, the convolutional neural network model 1000 includes three convolutional layers, two activation layers, and a cost layer. The convolutional layers are denoted as the Conv 1, the Conv 2, and the Conv 3. The activation layers are denoted as an activation function ReLU. The cost layer is denoted as a loss function MSE. The training process of the convolutional neural network model 1000 may include four stages, including feature extraction, non-linear mapping, reconstruction, and optimization stages.

Figure 11:
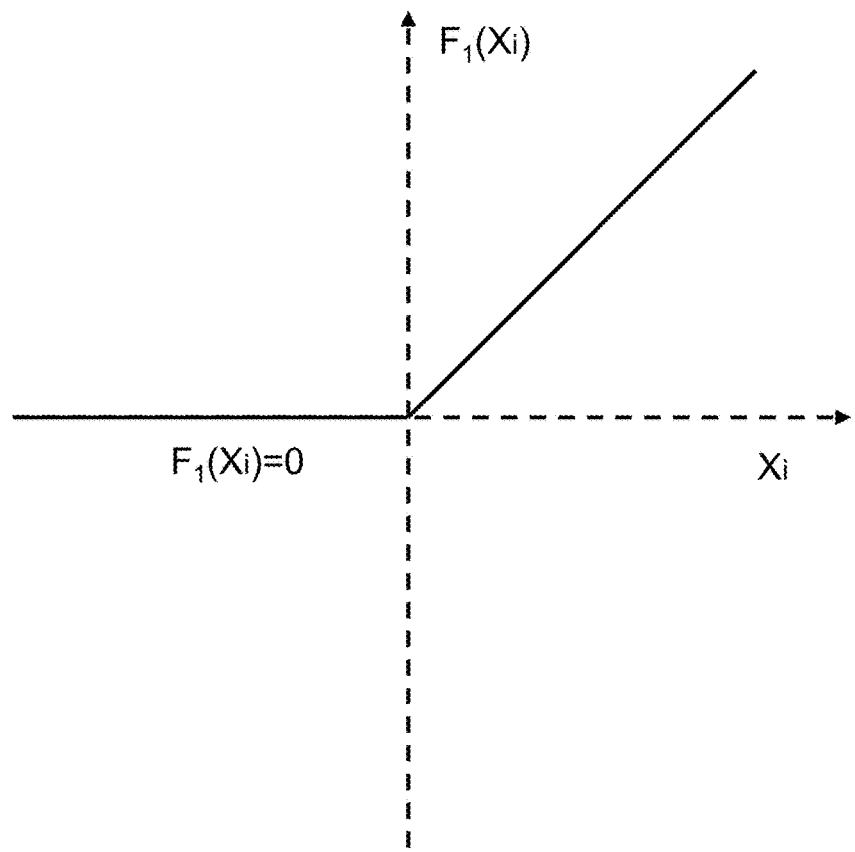
FIG. 11 shows an exemplary relationship between feature values and data blocks according to some embodiments of the present disclosure.

During the feature extraction stage, the input data (e.g., the one or more first data blocks, the first gradient information described in FIG. 8) may be input into the convolutional layer Conv 1, during which the features of the input data may be extracted. Then the activation function may perform a non-linear operation on the outputted features from the convolutional layer Conv 1. Exemplary techniques of performing a non-linear operation based on an activation function may be found in, for example, a literature entitled "RECTIFIED LINEAR UNITS IMPROVE RESTRICTED BOLTZMANN MACHINES" published on "Proceedings of the 27th International Conference on Machine Learning" on 2010, the contents of which are hereby incorporated by reference. Merely by way of example, for a first data block of the input data, the feature(s) may be extracted according to Equation (6) as below:

$$F_1(X_i) = \max(0, W_1 * X_i + B_1), \qquad (6)$$

wherein $X_i$ refers to the $i^{th}$ first data block of the input data; $W_1$ refers to a first filter; $B_1$ refers to a first deviation; * refers to a convolution operation; and $F_1(X_i)$ refers to the feature value(s) extracted from the $i^{th}$ first data block $X_i$. The size of the first filter $W_1$ may be equal to $c \times f_1 \times f_1$ in which c refers to the number of channels in the input data and $f_1$ refers to the spatial size of the first filter(s). An exemplary relationship between the feature values $F_1(X_i)$ and the first data block $X_i$ is shown in FIG. 11. The abscissa represents first data block(s), and the ordinate represents extracted feature value(s) of the first data block(s). As shown in FIG. 11, the feature value(s) may be equal to or larger than zero.

In some embodiments, a plurality of first filters may be used in the feature extraction to extract various features. For example, $n_1$ first filters may be used to extract $n_1$ features of each first data block. The extracted $n_1$ features of a first data block may be expressed by a $n_1$-dimensional feature vector. In the non-linear mapping part of the training process, the $n_1$-dimensional feature vector may be inputted into the convolutional layer Conv 2, after which a convolution operation (by the convolutional layer Conv 2) and an activation operation (by the activation function ReLU) may be performed on the $n_1$-dimensional feature vector. Merely by way of example, for a first data block of the input data, the $n_1$-dimensional feature vector may be processed according to Equation (7) as below:

$$F_2(X_i) = \max(0, W_2 * F_1(X_i) + B_2), \qquad (7)$$

wherein $W_2$ refers to a second filter; $B_2$ refers to a second deviation; and $F_2(X_i)$ refers to the feature value(s) of the first data block $X_i$. The size of the second filter may be $c \times f_2 \times f_2$ in which $f_2$ refers to the spatial size of the second filter. The number of the second filters used in the non-linear mapping may be $n_2$. Accordingly, the $n_1$-dimensional feature vector outputted from the feature extraction may be transformed into a $n_2$-dimensional feature vector after the non-linear mapping. The $n_2$-dimensional feature vector may include feature value(s) of $n_2$ features of the first data block, which may be used to reconstruct an image.

In the reconstruction stage of the training process, a convolution operation may be performed on the $n_2$-dimensional feature vector of the first data block to generate an image corresponding the first data block. In some embodiments, the image corresponding to the first data block may be regarded as an actual output of the first data block generated by the convolutional neural network model 1000. Merely by way of example, the reconstruction of the image may be performed according to Equation (8) as below:

$$F(X_i) = W_3 * F_2(X_i) + B_3, \qquad (8)$$

wherein $W_3$ refers to a third filter (e.g., a linear filter); $B_3$ refers to a third deviation; and $F(X_i)$ refers to the reconstructed image corresponding to the $i^{th}$ first data block of the input data. The size of the third filter may be $c \times f_3 \times f_3$ in which $f_3$ refers to the spatial size of the third filter. In some embodiments, $n_2$ third filters may be used in the image reconstruction.

In the optimization stage of the training process, an MSE may be determined to measure the similarity (or the difference) of the reconstructed data (e.g., one or more reconstructed images corresponding to first data blocks) and the tag data (e.g., one or more second data blocks). The preliminary parameter(s) of the convolutional neural network model may be adjusted based on the determined MSE. Details regarding the cost layer and the loss function may be found elsewhere in the present disclosure (e.g., FIGS. 9A and 9B, and the relevant descriptions thereof).

It should be noted that the example illustrated in FIGS. 10 and 11, and the descriptions thereof are provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. For example, the convolutional neural network model 1000 may include any number of convolutional layers other than three. As another example, the convolutional neural network model 1000 may adopt another activation function in the activation layer and/or another loss function in the lost layer. In some embodiments, the convolutional neural network model 1000 may be a denoising convolutional neural network (DCNN) model further including one or more normalization layers.

Figure 12:
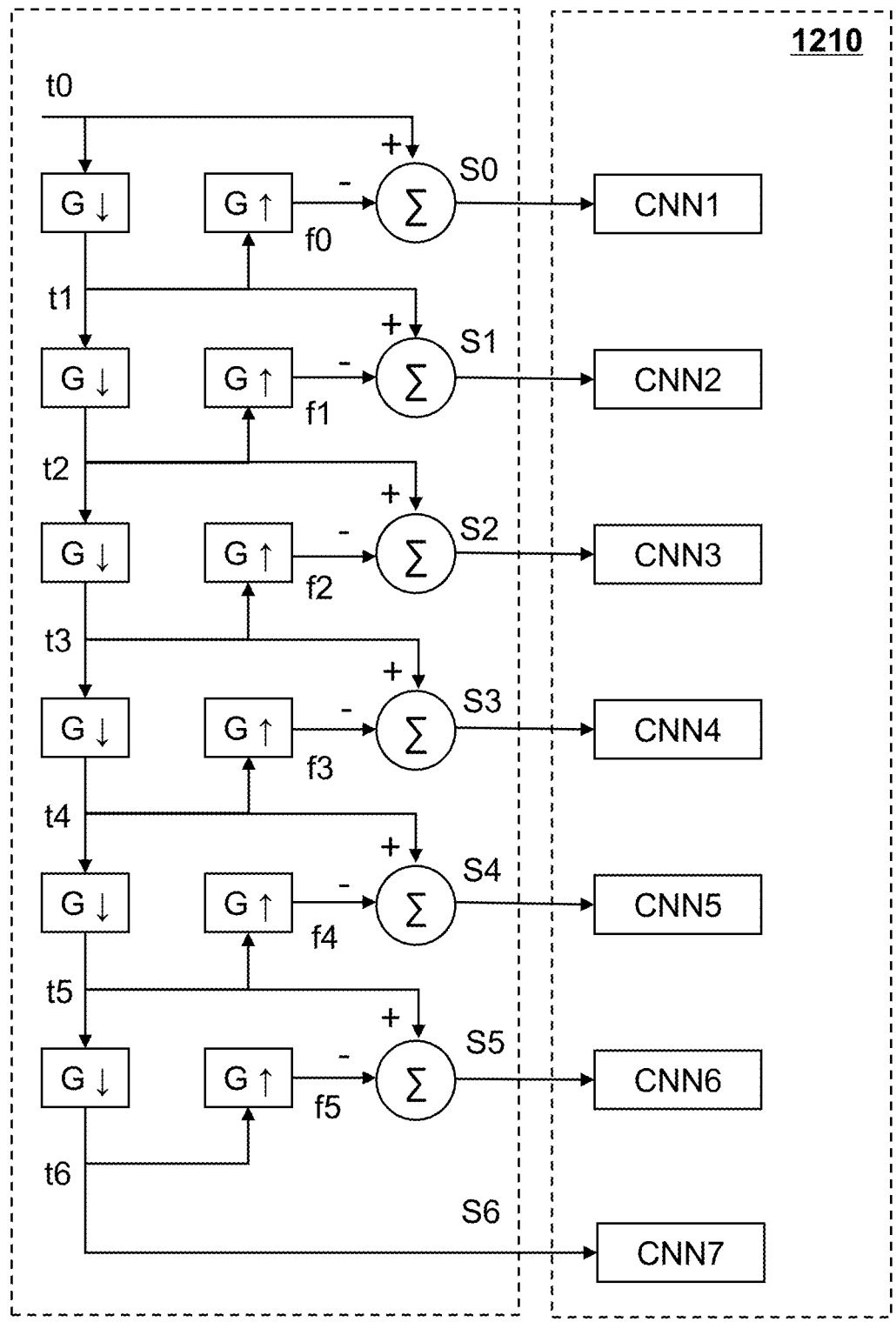
FIG. 12 is a schematic diagram illustrating image decomposition according to some embodiments of the present disclosure.

FIG. 12 is a schematic diagram illustrating image decomposition according to some embodiments of the present disclosure. As described in connection with FIG. 6, a first image and a second image may be decomposed into a plurality of sets of decomposition data. The sets of decomposition data may further be used for training one or more neural network model for scattering correction.

For illustration purposes only, the decomposition of an image t0 is described below as an example. In some embodiments, the image t0 may be an exemplary first image that includes scattering noises as described in connection with FIGS. 5 and 6. As shown in FIG. 12, the image t0 is decomposed into seven sets of decomposition data, including S0, S1, S2, S3, S4, S5, and S6. The seven sets of decomposition data may correspond to different frequency bands in which the decomposition data S0 corresponds to the highest frequency band and the decomposition data S6 corresponds to the lowest frequency band. "G↓" represents a down-sampling operation. For example, image t1 is determined by performing a down-sampling operation on the image t0. Similarly, images t2, t3, t4, t5, and t6 are determined by performing a down-sampling operation on the images t1, t2, t3, t4, and t5, respectively. "G↑" represents an up-sampling operation. For example, image f5 is determined by performing an up-sampling operation on the image t6. Similarly, images f4, f3, f2, f1, and f0 are determined by performing an up-sampling operation on the images t5, t4, t3, t2, and t1, respectively.

The sets of decomposition data S0 to S6 may be determined based on the up-sampled and down-sampled images. As shown in FIG. 12, the decomposition data S0 is a difference image between the images f0 and the image t0. The decomposition data S1 is a difference image between the images f1 and the image t1. The decomposition data S2 is a difference image between the images f2 and the image t2. The decomposition data S3 may is a difference image between the images f3 and the image t3. The decomposition data S4 is a difference image between the images f4 and the image t4. The decomposition data S5 is a difference image between the images f5 and the image t5. The decomposition data S6 is the image t6. A difference image between two images may be determined by subtracting one image from another.

In some embodiments, the sets of decomposition data S0 to S6 may be used to train a multi-scale convolutional neural network model. The multi-scale convolutional neural network model may include a plurality of sub-convolutional neural network models. For example, as illustrated in FIG. 12, a multi-scale convolutional neural network model 1210 includes seven sub-convolutional neural networks (illustrated as CNN1, CNN2, CNN3, CNN4, CNN5, CNN6, and CNN7 in FIG. 12). The sets of decomposition data S0 to S6 may be respectively inputted into the CNN1 to CNN7. During the training process, the preliminary parameter(s) of each sub-convolutional neural network model may be adjusted to generate corresponding model parameter(s). A plurality of trained sub-convolutional neural network models may be determined based on the sub-convolutional neural network models and their corresponding model parameters. Details regarding the training of a convolutional neural network model may be found elsewhere in the present disclosure (e.g., step 560 of the process 500, FIGS. 7 to 10, and the relevant descriptions thereof). In some embodiments, the trained sub-convolutional neural network models may be used to correct images (or a portion thereof) that correspond to different frequency bands, since they are respectively trained according to sets of decomposition data that correspond to different frequency bands.

Figure 13:
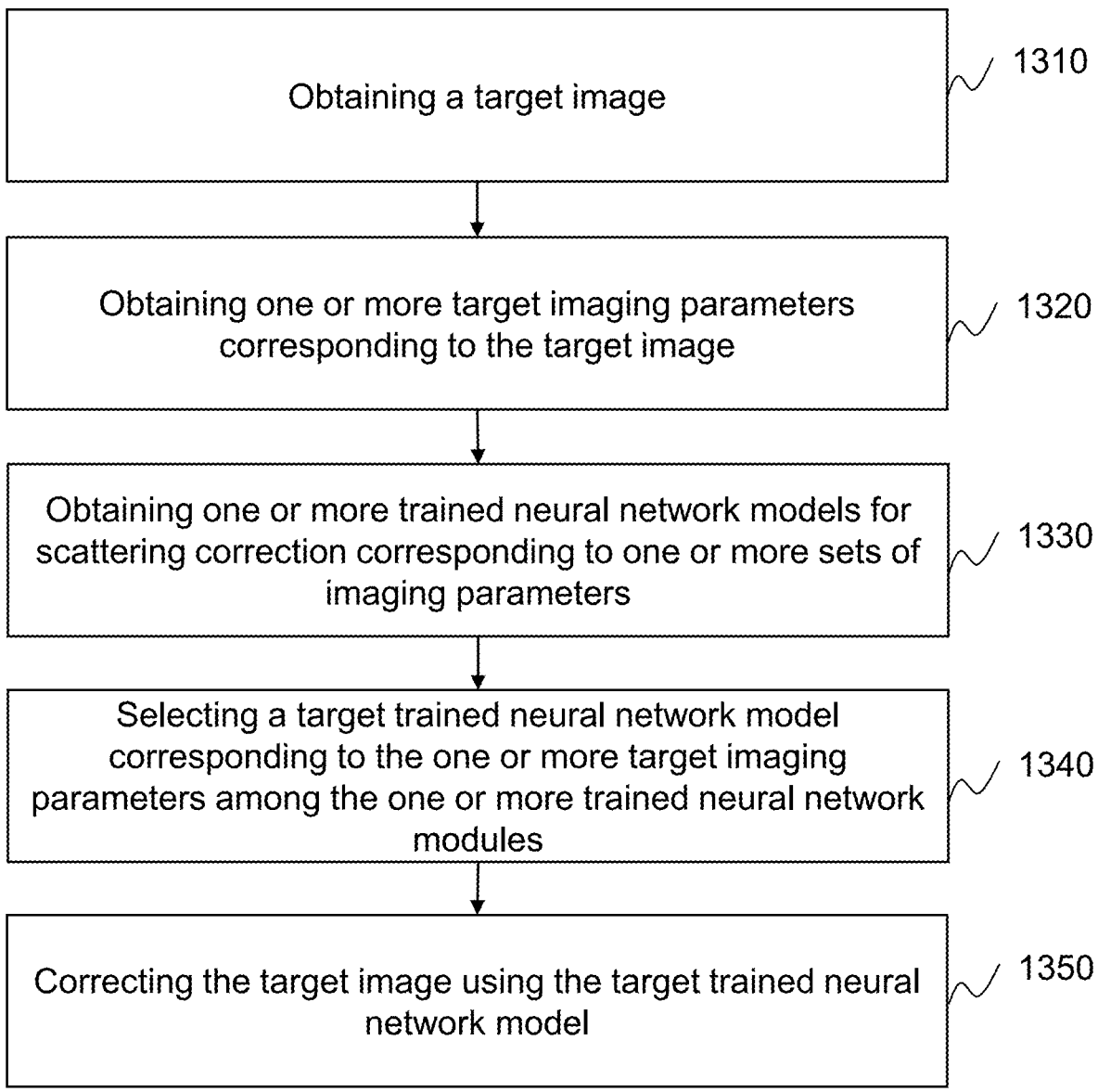
FIG. 13 is a flowchart illustrating an exemplary process for correcting a target image according to some embodiments of the present disclosure.

FIG. 13 is a flowchart illustrating an exemplary process for correcting a target image according to some embodiments of the present disclosure. The process 1300 may be implemented in the imaging system 100 illustrated in FIG. 1. For example, the process 1300 may be stored in the storage device 150 and/or the storage 220 in the form of instructions (e.g., an application), and invoked and/or executed by the processing device 140 (e.g., the processor 210 illustrated in FIG. 2, or one or more modules in the processing device 140-C illustrated in FIG. 4C). The operations of the illustrated process presented below are intended to be illustrative. In some embodiments, the process 1300 may be accomplished with one or more additional operations not described, and/or without one or more of the operations discussed. Additionally, the order in which the operations of the process 1300 as illustrated in FIG. 13 and described below is not intended to be limiting.

In 1310, the obtaining module 450 may obtain a target image. The target image may be an image including scattering noises. For example, the target image may be generated according to scan data acquired by the imaging device 110 without the grid. In some embodiments, the obtaining module 450 may obtain the target image from one or more components of the imaging system 100, such as the imaging device 110, a storage device (e.g., the storage device 150), and/or an external source.

In some embodiments, the target image may further be processed by, such as the processing device 140-C. The processing of the target image may include an image rotation, an image flipping, an image normalization, an image enhancement, an image filtering, or the like, or any combination thereof. For example, the target image may be flipped horizontally, vertically, or in any other direction. Alternatively or additionally, the target image may be rotated by an angel. In some embodiments, the target image may be normalized with respect to its range of pixel values according to a normalization technique. Details regarding the image processing (e.g., the image flipping, the image rotation, the image normalization) may be found elsewhere in the present disclosure (e.g., steps 530 and 540 of the process 500, and the relevant descriptions thereof).

In 1320, the obtaining module 450 may obtain one or more target imaging parameters corresponding to the target image. The target imaging parameters may refer to imaging parameters under which the target image is generated. Exemplary target imaging parameters may include a tube voltage, a tube current, a scanning time, an irradiation dose, a slice thickness of scanning, or the like, or any combination thereof. In some embodiments, the obtaining module 450 may obtain the target imaging parameter(s) from one or more components of the imaging system 100 (e.g., the imaging device 110, the storage device 150), and/or an external source.

In 1330, the obtaining module 450 may obtain one or more trained neural network models for scattering correction corresponding to one or more sets of imaging parameters. In some embodiments, the trained neural network models corresponding to various sets of imaging parameters may respectively be generated according to the process 500. Each of the trained neural network models may correspond to a set of imaging parameters. The trained neural network models may be obtained from an external source and/or one or more components of the imaging system 100, such as a processing device (e.g., the processing device 140-B), a storage device (e.g., the storage device 150).

In 1340, the selection module 460 may select a target trained neural network model corresponding to the target imaging parameters among the obtained trained neural network models. For example, the selection module 460 may compare the target imaging parameters with the one or more sets of imaging parameters, and determine a set of imaging parameters that has the smallest difference with the target imaging parameters. The difference between two sets of imaging parameters may be measured by, for example, a total difference, average difference, or median value of differences between values of each target imaging parameter and a corresponding image parameter.

In 1350, the correction module 470 may correct the target image using the target trained neural network model. In some embodiments, the correction module 470 may input the target image into the target trained neural network model to generate a corrected image. The corrected image may include less scattering noises than the target image.

In some embodiments, the target image may be normalized before being inputted into the target trained neural network model. The correction module 470 may input the normalized target image into the target trained neural network model to generate a corrected image. The correction module 470 may further perform an inverse normalization on the corrected image. For example, if the target image is normalized according to Equation (1) as described in connection with step 530 of the process 500, the pixel value of each pixel in the corrected image may be inversely normalized by multiplying $(I_{max}-I_{min})$ and then adding $I_{min}$. As another example, if the target image is normalized according to Equation (2) as described in connection with step 530 of the process 500, the pixel value of each pixel in the corrected image may be inversely normalized by multiplying $nI_v$ and then adding $I_a$.

In some embodiments, the target trained neural network model may be a trained multi-scale convolutional neural network model that includes a plurality of trained sub-convolutional neural network models. The trained sub-convolutional neural network models may correspond to a plurality of frequency bands as described elsewhere in this disclosure (e.g., FIG. 12 and the relevant descriptions). To correct the target image based on the multi-scale convolutional neural network model, the correction module 470 may decompose the target image into a plurality of decomposed target images. The decomposed target images may correspond to the same or substantially same frequency bands as the sub-convolutional neural network models. Each decomposed target image may be inputted into a trained sub-convolutional neural network model that corresponds to the same or substantially frequency band to generate a corrected decomposed image. The correction module 470 may further generate a corrected target image based on the plurality of corrected decomposed target images. For example, the corrected decomposed target images may be combined into the corrected target image according to an image blending technique (e.g., a Laplacian blending technique, a Gaussian blending technique). Details regarding the combination of corrected decomposed target images may be found elsewhere in this disclosure (e.g., FIG. 14 and the relevant descriptions).

Figure 14:
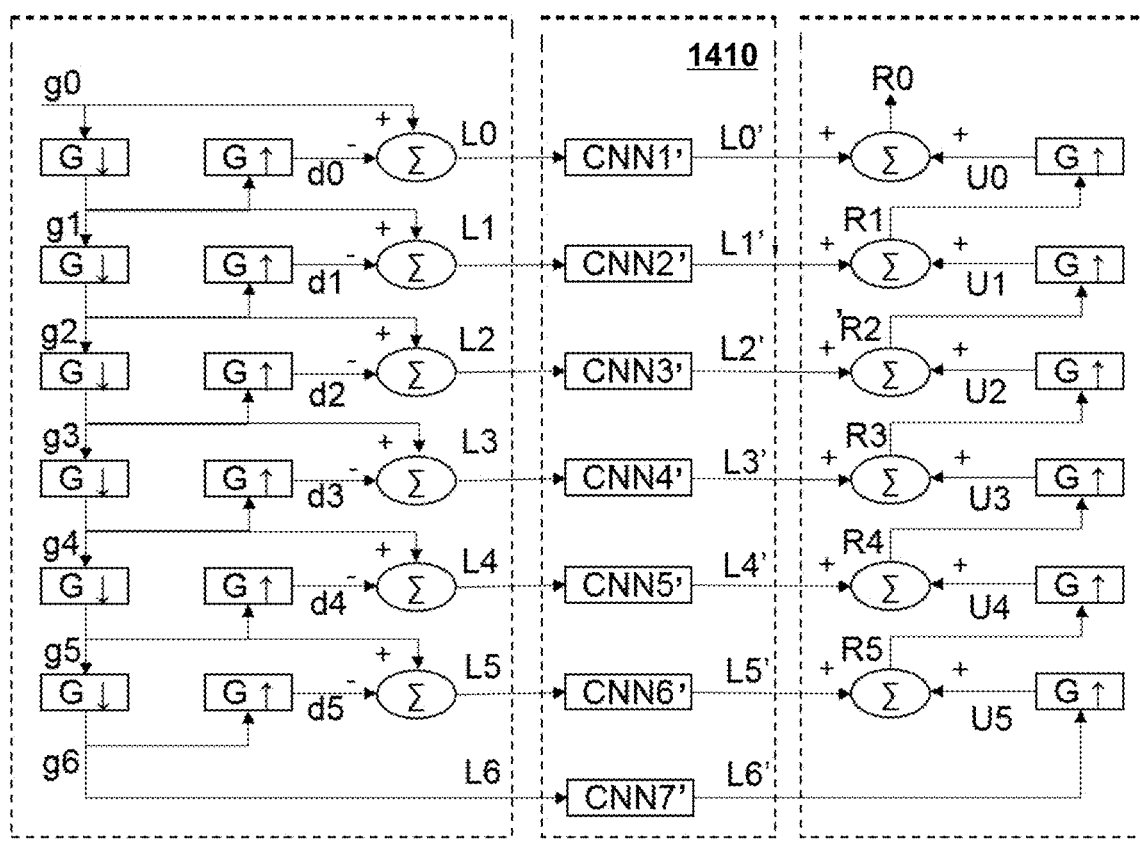
FIG. 14 shows a schematic diagram for correcting a target image based on a trained multi-scale convolutional neural network model according to some embodiments of the present disclosure.

FIG. 14 shows a schematic diagram for correcting a target image g0 based on a trained multi-scale convolutional neural network model 1410 according to some embodiments of the present disclosure. The trained multi-scale convolutional neural network model 1410 includes seven trained sub-convolutional neural network models (i.e., CNN1', CNN2', CNN3', CNN4', CNN5', CNN6', and CNN7' as shown in FIG. 14). The trained sub-convolutional neural network models may correspond to various frequency bands. In some embodiments, the trained multi-scale convolutional neural network model 1410 may be an exemplary trained neural network model for scattering correction. The trained multi-scale convolutional neural network model 1410 may be generated according to exemplary model training techniques described in the present disclosure (e.g., the process 500 and/or FIG. 12).

The target image g0 may be decomposed into a plurality of decomposed target images corresponding to the same or substantially same frequency bands as the trained sub-convolutional neural network models. Each decomposed target image may further be inputted into a corresponding trained sub-convolutional neural network mode for correction.

For example, as illustrated in FIG. 14, the target image g0 is decomposed into seven decomposed target images; that is, L0, L1, L2, L3, L4, L5, and L6. The decomposed target images L0 to L6 respectively correspond to the same or substantially same frequency band as the trained sub-convolutional neural network models CNN1' to CNN7'. The decomposition of the target image g0 may be performed in a similar manner as that of the first image t0, and the descriptions thereof are not repeated here. The decomposed target images L0 to L6 are respectively inputted into the trained sub-convolutional neural network models CNN1' to CNN7' to generate corrected decomposed target images L0' to L6'.

After the correction of the decomposed target images, a corrected target image may be generated based on the corrected decomposed target images. For example, the corrected target image may be generated based on an image blending technique. As shown in FIG. 14, image U5 may be generated by performing an up-sampling operation on the corrected decomposed target image L6'. The image U5 may further be added with the corrected decomposed target image L5' to generate an image R5. Image U4 may be determined by performing an up-sampling operation on the image R5. The image U4 may further be added with the corrected decomposed target image L4' to generate an image R4. Image U3 may be determined by performing an up-sampling operation on the image R4. The image U3 may further be added with the corrected decomposed target image L3' to generate an image R3. Image U2 may be determined by performing an up-sampling on the image R3. The image U2 may further be added with the corrected decomposed target image L2' to generate an image R2. Image U1 may be determined by performing an up-sampling on the image R2. The image U1 may further be added with the corrected decomposed target image L1' to generate an image R1. Image U0 may be determined by performing an up-sampling operation on the image R1. The image U0 may further be added with the corrected decomposed target image L0' to generate an image R0. The image R0 may be the target image after the correction (also referred to herein as the corrected target image).

It should be noted that the above example illustrated in FIG. 14 and the descriptions thereof are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the trained multi-scale convolutional neural network model 1410 may include any number of trained sub-convolutional neural network models, and the target image may be decomposed into any number of decomposed target images. As another example, the corrected target image may be generated based on the corrected decomposed target images according to any other suitable image blending technique.

FIG. 15A shows an exemplary image 1500A according to some embodiments of the present disclosure. FIG. 15B shows an exemplary corrected image 1500B according to some embodiments of the present disclosure. The corrected image 1500B is generated by correcting the image 1500A according to exemplary image correction techniques disclosed in the present disclosure (e.g., the process 1300). As illustrated, the corrected image 1500B includes less scattering noises than the image 1500A. The contrast between the spine 1510 and the lungs 1520 in the corrected image 1500B are higher than that in the image 1500B.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system, comprising:
a storage device storing a set of instructions; and
at least one processor configured to communicate with the storage device, wherein when executing the set of instructions, the at least one processor is configured to direct the system to:
generate a trained neural network model for scattering correction corresponding to one or more imaging parameters, wherein the trained neural network model is trained using training data, the training data including at least one first set of training data, the first set of training data being generated according to a process for generating the first set of training data, the process including:
obtaining a first image corresponding to the one or more imaging parameters;
obtaining a second image, the second image including less scattering noises than the first image; and
determining, based on the first image and the second image, the first set of training data.

2. The system of claim 1, wherein:
the second image is generated according to second scan data acquired by an imaging device configured with a grid under the one or more imaging parameters, and the first image is generated according to first scan data acquired by the imaging device without the grid under the one or more imaging parameters, or
the first image is generated according to the first scan data acquired by the imaging device without the grid under the one or more imaging parameters, and the second image is generated based on the first image by removing at least some of the scattering noises of the first image, or
the first image and the second image are simulated according to a Monte-Carlo technique under the one or more imaging parameters.

3. The system of claim 1, wherein determining the first set of training data based on the first image and the second image further comprises:
processing the first image;
processing the second image; and
determining, based on the processed first image and the processed second image, the first set of training data.

4. The system of claim 1, wherein:
the first set of training data includes input data and tag data, and
determining the first set of training data based on the first image and the second image further comprises:
selecting a first sub-area from the first image;
designating image data related to the first sub-area as the input data;
selecting, from the second image, a second sub-area corresponding to the first sub-area; and
designating image data related to the second sub-area as the tag data.

5. The system of claim 1, wherein to generate the trained neural network model for scattering correction, the at least one processor is further configured to direct the system to:
acquire a preliminary neural network model;
determine, by inputting the training data into the preliminary neural network model, one or more model parameters; and
determine, based on the one or more model parameters and the preliminary neural network model, the trained neural network model.

6. The system of claim 1, wherein determining the first set of training data based on the first image and the second image further comprises:
decomposing the first image into a plurality of sets of first decomposition data;
decomposing the second image into a plurality of sets of second decomposition data, the number of the plurality of sets of first decomposition data being equal to the number of the plurality of sets of second decomposition data;
generating, based on the plurality of sets of first decomposition data and the plurality of sets of second decomposition data, a plurality of matching pairs of decomposition data, each of the plurality of matching pairs of decomposition data including a set of first decomposition data and a corresponding set of second decomposition data; and
determining, based on one of the plurality of matching pair of decomposition data, the first set of training data.

7. The system of claim 6, wherein:
the decomposing of the first image is performed according to a frequency of at least one of the first image or image data related to the first image, and
the decomposing of the second image is performed according to a frequency of at least one of the second image or image data related to the second image.

8. The system of claim 6, wherein:
the decomposing of the first image is performed according to at least one of a wavelet decomposition technique or a Laplacian decomposition technique, and the decomposing of the second image is performed according to at least one of the wavelet decomposition technique or the Laplacian decomposition technique.

9. The system of claim 6, wherein:
the plurality of sets of first decomposition data include a plurality of first decomposed images corresponding to a plurality of frequency bands,
the plurality of sets of second decomposition data include a plurality of second decomposed images corresponding to the plurality of frequency bands, and wherein
to generate the trained neural network model for scattering correction, the at least one processor is further configured to direct the system to:
 determine, for each of the plurality of frequency bands, a relationship between a first decomposed image corresponding to the frequency band and a second decomposed image corresponding to the frequency band; and
 determine the trained neural network model for scattering correction based on the determined relationships for the plurality of frequency bands.

10. A system, comprising:
a storage device storing a set of instructions; and
at least one processor configured to communicate with the storage device, wherein when executing the set of instructions, the at least one processor is configured to direct the system to:
 obtain a target image;
 obtain one or more target imaging parameters corresponding to the target image;
 obtain one or more trained neural network models for scattering correction corresponding to one or more sets of imaging parameters;
 select, among the one or more trained neural network models for scattering correction, a target trained neural network model for scattering correction corresponding to the one or more target imaging parameters; and
 correct, using the target trained neural network model for scattering correction, the target image.

11. The system of claim 10, wherein one of the one or more trained neural network model for scattering correction is trained using training data, the training data including at least one first set of training data, the first set of training data being generated by a process for generating the first set of training data, the process including:
 obtaining a first image corresponding to the one or more imaging parameters;
 obtaining a second image, the second image including less scattering noises than the first image; and
 determining, based on the first image and the second image, the first set of training data.

12. The system of claim 10, wherein to correct the target image, the at least one processor is further configured to direct the system to:
 decompose the target image into a plurality of decomposed target images corresponding to a plurality of frequency bands;
 correct, based on the target trained neural network model, the plurality of decomposed target images; and
 generate the corrected target image based on the plurality of corrected decomposed target images.

13. The system of claim 11, wherein determining the first set of training data based on the first image and the second image further comprises:
 decomposing the first image into a plurality of sets of first decomposition data;
 decomposing the second image into a plurality of sets of second decomposition data, the number of the plurality of sets of first decomposition data being equal to the number of the plurality of sets of second decomposition data;
 generating, based on the plurality of sets of first decomposition data and the plurality of sets of second decomposition data, a plurality of matching pairs of decomposition data, each of the plurality of matching pairs of decomposition data including a set of first decomposition data and a corresponding set of second decomposition data; and
 determining, based on one of the plurality of matching pair of decomposition data, the first set of training data.

14. A method implemented on a computing device including a storage device and at least one processor, comprising:
 generating a trained neural network model for scattering correction corresponding to one or more imaging parameters, wherein the trained neural network model is trained using training data, the training data including at least one first set of training data, the first set of training data being generated according to a process for generating the first set of training data, the process including:
 obtaining a first image corresponding to the one or more imaging parameters;
 obtaining a second image, the second image including less scattering noises than the first image; and
 determining, based on the first image and the second image, the first set of training data.

15. The method of claim 14, wherein determining the first set of training data based on the first image and the second image further comprises:
 processing the first image;
 processing the second image; and
 determining, based on the processed first image and the processed second image, the first set of training data.

16. The method of claim 14, wherein:
the first set of training data includes input data and tag data, and
determining the first set of training data based on the first image and the second image further comprises:
 selecting a first sub-area from the first image;
 designating image data related to the first sub-area as the input data;
 selecting, from the second image, a second sub-area corresponding to the first sub-area; and
 designating image data related to the second sub-area as the tag data.

17. The method of claim 14, wherein the generating the trained neural network model for scattering correction further comprises:
 acquiring a preliminary neural network model;
 determining, by inputting the training data into the preliminary neural network model, one or more model parameters; and
 determining, based on the one or more model parameters and the preliminary neural network model, the trained neural network model.

18. The method of claim 17, wherein the first set of training data includes input data and tag data, and the one or more model parameters include a relationship between the input data and the tag data, and
the determining the one or more model parameters further comprises:
 dividing the input data into a plurality of first data blocks;

dividing the tag data into a plurality of second data blocks corresponding to the plurality of first data blocks;

determining first gradient information of the first data blocks;

determining second gradient information of the second data blocks; and determining, based on the first gradient information and the second gradient information, the relationship between the input data and the tag data.

19. The method of claim 14, wherein determining the first set of training data based on the first image and the second image further comprises:

decomposing the first image into a plurality of sets of first decomposition data;

decomposing the second image into a plurality of sets of second decomposition data, the number of the plurality of sets of first decomposition data being equal to the number of the plurality of sets of second decomposition data;

generating, based on the plurality of sets of first decomposition data and the plurality of sets of second decomposition data, a plurality of matching pairs of decomposition data, each of the plurality of matching pairs of decomposition data including a set of first decomposition data and a corresponding set of second decomposition data; and determining, based on one of the plurality of matching pair of decomposition data, the first set of training data.

20. The method of claim 19, wherein:

the decomposing of the first image is performed according to a frequency of at least one of the first image or image data related to the first image, and the decomposing of the second image is performed according to a frequency of at least one of the second image or image data related to the second image.

* * * * *